US006852113B2

(12) United States Patent
Nathanson et al.

(10) Patent No.: US 6,852,113 B2
(45) Date of Patent: Feb. 8, 2005

(54) INTERNAL OSTEOTOMY FIXATION DEVICE

(75) Inventors: Jeremy J. Nathanson, Vista, CA (US); Dylann D. Ceriani, San Diego, CA (US); Richard Gildersleeve, Escondido, CA (US); Daniel S. Pflaster, Carlsbad, CA (US); David L. Churchill, Burlington, VT (US); Stephen J. Incavo, South Burlington, VT (US); Bruce D. Beynnon, South Burlington, VT (US)

(73) Assignee: Orthopaedic Designs, LLC, Burlington, VT (US)

( * ) Notice: Subject to any disclaimer, the term of this patent is extended or adjusted under 35 U.S.C. 154(b) by 123 days.

(21) Appl. No.: 10/021,980

(22) Filed: Dec. 14, 2001

(65) Prior Publication Data

US 2003/0114856 A1 Jun. 19, 2003

(51) Int. Cl.[7] .............................................. A61B 17/80
(52) U.S. Cl. .............................. 606/71; 606/69; 606/73
(58) Field of Search ............................. 606/70, 71, 72, 606/73, 69, 61, 60, 54, 56, 55, 57, 58, 59

(56) References Cited

U.S. PATENT DOCUMENTS

| 3,659,595 | A | 5/1972 | Haboush |
| 4,157,715 | A | 6/1979 | Westerhoff |
| 5,122,140 | A | 6/1992 | Asche et al. |
| 5,364,396 | A | 11/1994 | Robinson et al. |
| 5,484,439 | A | 1/1996 | Olson et al. |
| 5,501,684 | A | 3/1996 | Schlapfer et al. |
| 5,620,448 | A | 4/1997 | Puddu |
| 5,626,581 | A | 5/1997 | Staehlin et al. |
| 5,672,177 | A | 9/1997 | Seldin |
| 5,681,313 | A | 10/1997 | Diez |
| 5,749,875 | A | 5/1998 | Puddu |
| 5,827,286 | A | 10/1998 | Incavo et al. |
| 6,036,690 | A | 3/2000 | De La Plaza Fernandez |
| 6,355,036 | B1 * | 3/2002 | Nakajima .................... 606/57 |

FOREIGN PATENT DOCUMENTS

FR        2 796 829        2/2001

OTHER PUBLICATIONS

Image of Orthopedic device display at http://www.anthony-k.com/images/os.jpg, prior to Mar. 18, 2002.
Image of Orthopedic device displayed at http://www.anthony-k.com/images/rond.jpg, prior to Mar. 18, 2002.
Image of Orthopedic device displayed at http://www.anthony-k.com/images/impl_pres.jpg, prior to Mar. 18, 2002.

* cited by examiner

Primary Examiner—Kevin Shaver
Assistant Examiner—Candice C. Stokes
(74) Attorney, Agent, or Firm—Greenberg Traurig, LLP

(57) ABSTRACT

An internal osteotomy fixation apparatus is provided. The device comprises a distal plate including a channel. A slide is slidably received within the channel such that the slide is translatable with respect to the distal plate along a first axis. A proximal plate is hingedly connected to the slide, such that the proximal plate has two degrees of freedom relative to the distal plate. A ledge protruding from a first portion of the proximal plate is configured to support a proximal bone segment when the device is implanted. The slide includes ratchet teeth. A ratchet arm including teeth is attached to the distal plate, and configured to engage the slide ratchet teeth. A cross-section of the ratchet arm is configured to maintain a constant stress level along a flexed portion of the arm. The distal plate includes a shelf upon which the ratchet arm rests. Compressive loads borne by the device are translated through the shelf to the distal plate. A minimum length of the device is related to the longer of the ratchet arm or the segment of teeth on the slide. The distal plate includes a hole through which a release mechanism is accessible.

24 Claims, 20 Drawing Sheets

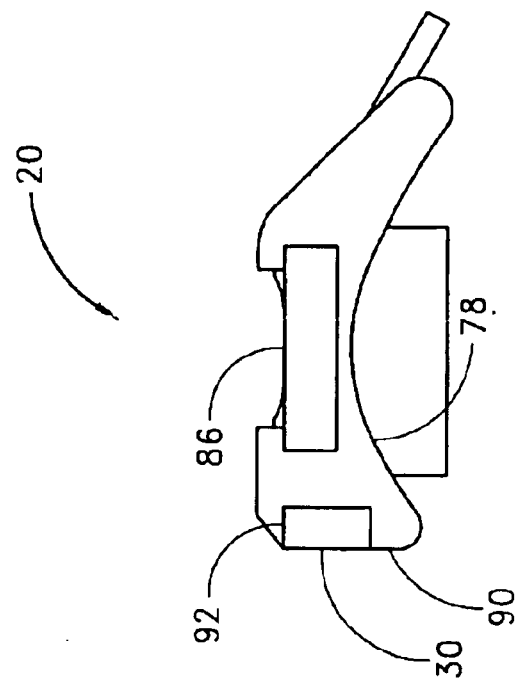
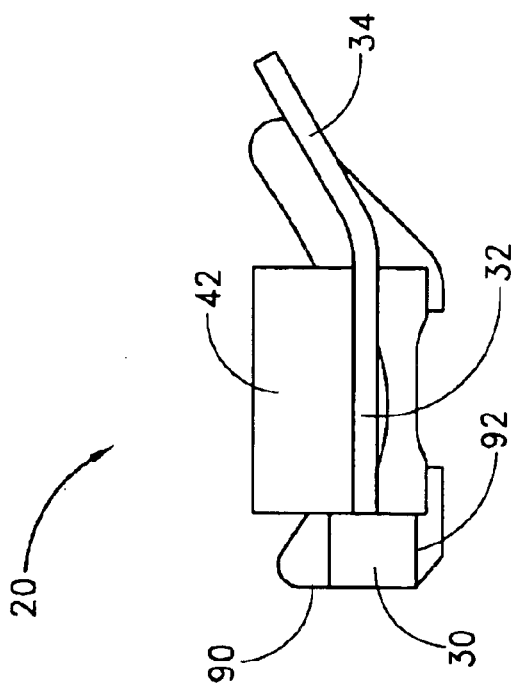

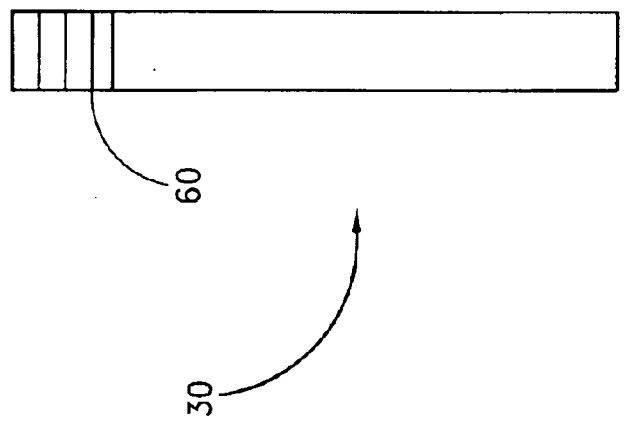
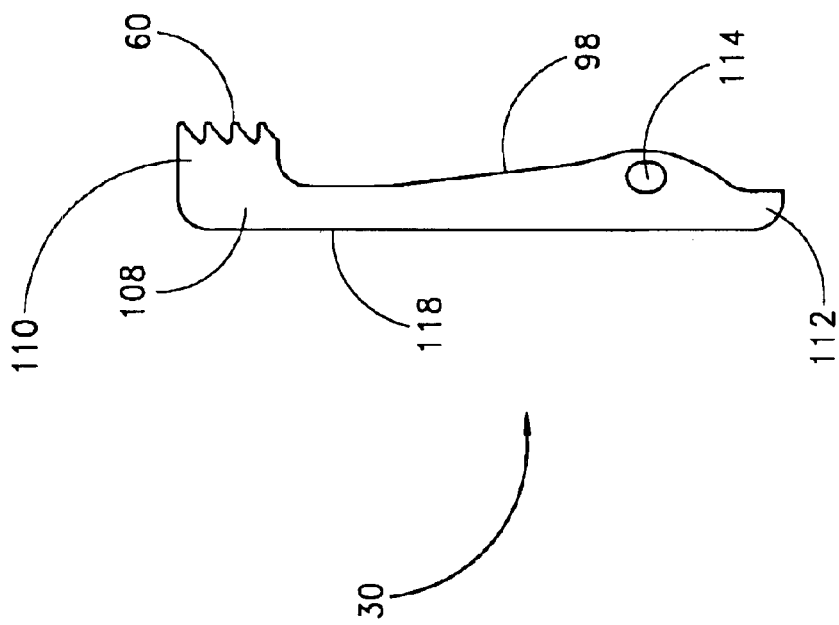

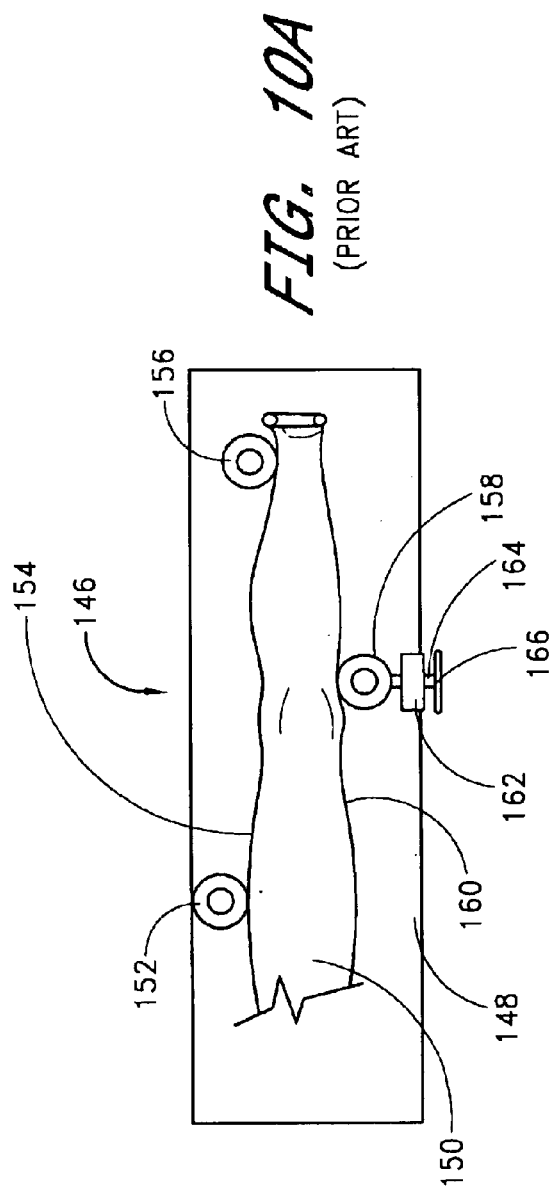
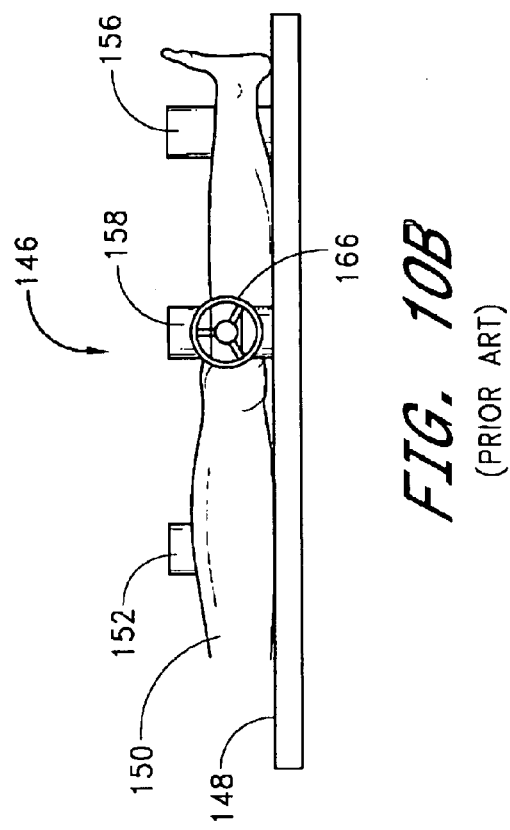

INTERNAL OSTEOTOMY FIXATION DEVICE

BACKGROUND OF THE INVENTION

1. Field of the Invention

The present invention relates to devices for performing an osteotomy. More particularly, preferred embodiments of the internal osteotomy fixation device cause minimal deformation of surrounding tissue and skin, are easy to implant, and are easy to manipulate after implantation.

2. Description of the Related Art

A high tibial osteotomy (HTO) is a procedure to correct misalignment of a lower limb due to the wear of cartilage in the knee or bone deformities. A HTO is usually performed to relieve pain from osteoarthritis. The procedure involves making an incision from the medial side of the upper tibia all the way across to the cortex on the lateral side. The incision is then opened into a wedge shape to change the alignment of the joint. An implant device holds the wedge open until it is filled in by new bone growth.

The HTO restores the proper anatomic and mechanical axes of the extremity. The operation is usually performed adjacent to the end of the tibia, without removing the articular (end) surface, as would be the case for preparation of the tibia for implantation of a joint prosthesis.

The angle correction necessary to achieve the proper reorientation is an important consideration in each HTO procedure. Determining this angle prior to or during the HTO procedure is often difficult. Therefore, the ability to adjust the implant device during the implantation procedure, and after the implantation procedure is complete, is very advantageous. Preferably such adjustment does not require further incisions or other invasions of the patient's body. Further, the tibia heals faster and causes less discomfort for the patient when the tibial incision is widened several times in small increments. Thus, prior art devices provide the capability to incrementally adjust the tibial incision using external adjustment means.

U.S. Pat. No. 5,827,286 (the '286 patent) discloses an incrementally adjustable tibial osteotomy fixation device and method. The device comprises a first plate member and a second plate member telescopically received within the first plate member. A proximal end of the first plate member includes a ratchet arm that extends toward a distal end of the first plate member. Teeth at a distal end of the ratchet arm cooperate with grooves on a face of the second plate member to allow advancement of the second plate member in a first direction. Lands on the opposite side of the teeth preclude movement of the second plate member in the opposite direction. Thus, the length of the fixation device can only be extended and not retracted. Both the first and second plates include screw holes through which bone screws extend in order to attach the plates to a tibia. The second plate member includes a bend near the proximal end that represents the general contour of the tibia.

When the device of the '286 patent is implanted, it is in its fully contracted position. The first plate member is secured to the tibia distal the tibial incision, while the second plate member is secured to the tibia proximal to the tibial incision. After completion of the implantation procedure, the wound and incision are allowed to heal for a few days to a few weeks. After proper healing, the physician gradually opens the tibial incision, thereby adjusting the angular orientation of the patient's tibia with respect to the rest of the leg.

To open the tibial incision, the physician incrementally lengthens the implant device. To incrementally lengthen the implant device, the physician places the patient in an external extension brace, which is illustrated in FIGS. 10A and 10B. The brace comprises three pads. A first pad is located on a first side of the patient's leg, which is the same side on which the device is located, proximal the device. The second pad is located on the same side of the patient's leg, distal the device. The third pad is located on the opposite side of the patient's leg, at about the same position as the device.

The first and second pads are stationary. The third pad is movable toward the patient's leg. With all three pads contacting the patient's leg, the physician urges the third pad further toward the patient's leg, thereby applying a bending load to the leg. The device is located at or near the point of maximum deflection, on the side of the leg that is placed in tension by the deflection. The tension widens the tibial incision and lengthens the device. When the physician removes the bending load from the patient's leg, the interaction of the ratchet teeth on the first plate member and the grooves on the second plate member prevents the device from contracting, or shortening in length. After allowing the incision to heal, the physician again lengthens the device in the same manner until the patient's leg reaches the proper angular alignment.

The device of the '286 patent, however, is not well suited for use in an osteotomy procedure. First, the device only allows for one degree of freedom, i.e. longitudinal extension. Thus, the device offers little flexibility in initially fitting the device to the patient's tibia. Furthermore, opening a tibial wedge creates motion in more than one direction. Not only do the proximal and distal edges of the wedge move apart, but the angular alignment of the proximal and distal bone segments changes. As the wedge is opened farther and farther, the device is not able to conform to the geometry of the opening wedge. The device thus creates stresses in the tibia that could lead to fracture.

Second, the device of the '286 patent locates the ratchet mechanism on the medial side of the implant. Therefore, the ratchet arm is stacked on top of the plate member including the grooves, which is in turn stacked on top of the tibia. The device thus protrudes a significant distance from the bone, causing unsightly deformation of the overlying skin and irritation to the patient.

Third, the configuration of the ratchet mechanism of the '286 device causes the device to be unnecessarily long. The ratchet design is essentially a lever spring with teeth at one end. The lever spring has a finite length, $L_1$. This length must be sufficient to impart enough flexibility to the ratchet to allow the teeth to pass over the grooves. The length, $L_2$, from the first, or most proximal groove, to the last, or most distal groove, determines the range of extension of the device. The ratchet teeth are distal to the ratchet. When the device is implanted, the entire groove portion is distal to the ratchet. Thus, the minimum total device length is the sum of $L_1$ and $L_2$. The device length could be reduced if the device could be arranged so that the minimum device length were equal to the greater of $L_1$ and $L_2$, rather than their sum.

Fourth, the ratchet arm is attached to the first plate member as a simple cantilevered beam. Thus, loads tending to retract the device are primarily shouldered by the ratchet arm. Intense loads could cause the arm to fail, forcing the patient to have to undergo the HTO procedure all over again. To avoid such a catastrophe, the ratchet arm instead must be built sturdily enough to handle these intense loads. Generally, however, the sturdier the arm must be, the larger it must be. And the larger the arm is, the more it causes unsightly deformation of the patient's skin and patient irritation.

Fifth, the ratchet arm has a simple rectangular cross-section along its entire length. Thus, because it is a cantilevered beam, during flexion the maximum stress in the ratchet arm occurs at the point where the ratchet arm is attached to the first plate member. The remainder of the arm's length is under relatively little stress. Therefore, the flexibility of the arm is limited, because relatively little deflection could cause the arm to undergo plastic deformation at the point of maximum stress. If the arm deforms plastically, its usefulness as a ratchet is severely diminished.

Sixth, the device of the '286 patent is rather difficult to retract after it has been implanted. The physician must make an incision in the patient's leg just distal of the distal end of the ratchet arm. He then inserts a tool similar to a crowbar and pries the ratchet away from the grooves. First, the incision that the physician must make in order to insert the crowbar is rather large. Second, the physician has to blindly feel his way through the incision to find the proper place on the ratchet to engage the end of the crowbar. Both of these features of the device are likely to cause unnecessary trauma to the patient's leg. Third, after the physician pries the device open with the crowbar, he or she must hold the crowbar in place with one hand while retracting the implant device with the other hand. This procedure requires a great deal of dexterity. If the crowbar slips, the patient may suffer further unnecessary trauma.

Seventh, the second plate member of the '286 device is attached to the proximal bone segment with only two bone screws inserted through two holes on the plate member. As the tibial incision is widened, the healing bone tissue within the incision is stretched. Thus, it tends to pull the incision closed. Each of the screws through the second plate member must shoulder half of the load imposed by the healing tissue. Not only is there a risk that the screws could pull out, but the stress concentrations in each location cause trauma to the bone tissue.

Therefore, an osteotomy fixation device that eliminates the negative features outlined above would be of great value to physicians and patients undergoing osteotomy procedures.

SUMMARY OF THE INVENTION

The preferred embodiments of the internal osteotomy fixation device have several features, no single one of which is solely responsible for their desirable attributes. Without limiting the scope of this internal osteotomy fixation device as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include proper conformity to the geometry of an opening bone wedge, flexibility in initially fitting the device to a patient's tibia, low profile, minimal overall length, transfer of applied loads to attachment plates, elimination of stress concentrations in the ratchet arm, easy retraction, and sturdy support of the proximal tibial segment.

A preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to the distal plate. The ratchet arm includes teeth configured to engage the slide ratchet teeth. A proximal plate is hingedly connected to the slide. Preferably the proximal plate has two degrees of freedom relative to the distal plate, translation along a longitudinal axis and rotation about a transverse axis.

Another preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to the distal plate. The ratchet arm includes teeth configured to engage the slide ratchet teeth. A proximal plate is connected to the slide. The proximal plate includes a first portion defining a first plane, and a ledge defining a second plane substantially perpendicular to the first plane. Preferably, a proximal surface of the ledge abuts a distal surface of a proximal bone segment when the device is implanted within a patient.

Another preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to the distal plate. The ratchet arm includes teeth configured to engage the slide ratchet teeth. The slide includes a first portion defining a first plane, and a ledge defining a second plane substantially perpendicular to the first plane. Preferably, a proximal surface of the ledge abuts a distal surface of a proximal bone segment when the device is implanted within a patient.

Another preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to the distal plate. The ratchet arm includes teeth configured to engage the slide ratchet teeth. A cross-sectional area of the ratchet arm decreases from a distal end of the ratchet arm toward a proximal end of the ratchet arm. Preferably, the ratchet arm is configured to maintain a constant stress level along a flexed portion of the ratchet arm. Also, the ratchet arm is preferably fixed to the distal plate in a cantilevered fashion.

Another preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to the distal plate. The ratchet arm includes teeth configured to engage the slide ratchet teeth. The distal plate includes a first surface comprising a shelf, which faces a proximal end of the device The ratchet arm includes a second surface, which faces a distal end of the device. The second surface abuts the shelf. Preferably, the second surface transmits compressive loads experienced by the device to the distal plate. In order to facilitate such transmission, preferably the ratchet arm further comprises an oval-shaped through hole in a distal portion, and a major axis of the oval is aligned with the first axis.

Another preferred embodiment of the internal osteotomy fixation device comprises a distal plate including a channel. A slide is slidably received within the channel such that the slide is translatable with respect to the distal plate along a first axis. The slide includes a segment of ratchet teeth on a first surface, and the segment has a first length. A ratchet arm, having a second length, is fixed to the distal plate. The ratchet arm includes teeth configured to engage the slide ratchet teeth. In a completely retracted configuration, the segment overlaps the ratchet arm such that an overall length of the device is dependent upon the longer of the first length or the second length.

Another preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to the distal plate in a cantilevered fashion. The ratchet arm includes teeth configured to engage the slide ratchet teeth. The distal plate further comprises a through-hole, and a release tool is insertable within the through-hole to engage the ratchet arm. Preferably, rotation of the release tool within the through-hole flexes the ratchet arm and disengages the ratchet arm teeth from the slide teeth. Also, the distal plate preferably further comprises a beveled portion surrounding a medial side of the through-hole, and the beveled portion is preferably configured to guide the release tool toward the through-hole.

Another preferred embodiment of the internal osteotomy fixation device comprises a distal plate including a channel. A slide is slidably received within the channel such that the slide is translatable with respect to the distal plate along a first axis. The slide includes ratchet teeth on a first surface. A ratchet arm is fixed to a posterior portion of the distal plate. The ratchet arm includes teeth configured to engage the slide ratchet teeth.

Another preferred embodiment of the internal osteotomy fixation device comprises a proximal plate including a channel. A slide is slidably received within the channel such that the slide is translatable with respect to the proximal plate along a first axis. The slide includes ratchet teeth on a first surface. A ratchet arm is fixed to the proximal plate. The ratchet arm includes teeth configured to engage the slide ratchet teeth. A distal plate is hingedly connected to the slide.

Another preferred embodiment of the internal osteotomy fixation device comprises a proximal plate including a channel. A slide is slidably received within the channel such that the slide is translatable with respect to the proximal plate along a first axis. The slide includes ratchet teeth on a first surface. A ratchet arm is fixed to the proximal plate. The ratchet arm includes teeth configured to engage the slide ratchet teeth. A cross-sectional area of the ratchet arm decreases from a proximal end of the ratchet arm toward a distal end of the ratchet arm. Preferably, the ratchet arm is configured to maintain a constant stress level along a flexed portion of the ratchet arm.

BRIEF DESCRIPTION OF THE DRAWINGS

The preferred embodiments of the internal osteotomy fixation device, illustrating its features, will now be discussed in detail. These embodiments depict the novel and non-obvious internal osteotomy fixation device shown in the accompanying drawings, which are for illustrative purposes only. These drawings include the following figures, in which like numerals indicate like parts:

FIG. 3A is a top plan view of the internal osteotomy fixation device of FIG. 1;

FIG. 3B is a bottom plan view of the internal osteotomy fixation device of FIG. 1;

FIG. 6A is a front elevation view of the ratchet arm of the internal osteotomy fixation device of FIG. 1;

FIG. 6B is a right-side elevation view of the ratchet arm of FIG. 6A;

FIG. 10A is a top plan view of a prior art external brace that is useful for extending the internal osteotomy fixation device of FIG. 1;

FIG. 10B is a front elevation view of the brace of FIG. 10A;

DETAILED DESCRIPTION OF THE PREFERRED EMBODIMENTS

Figure 1:
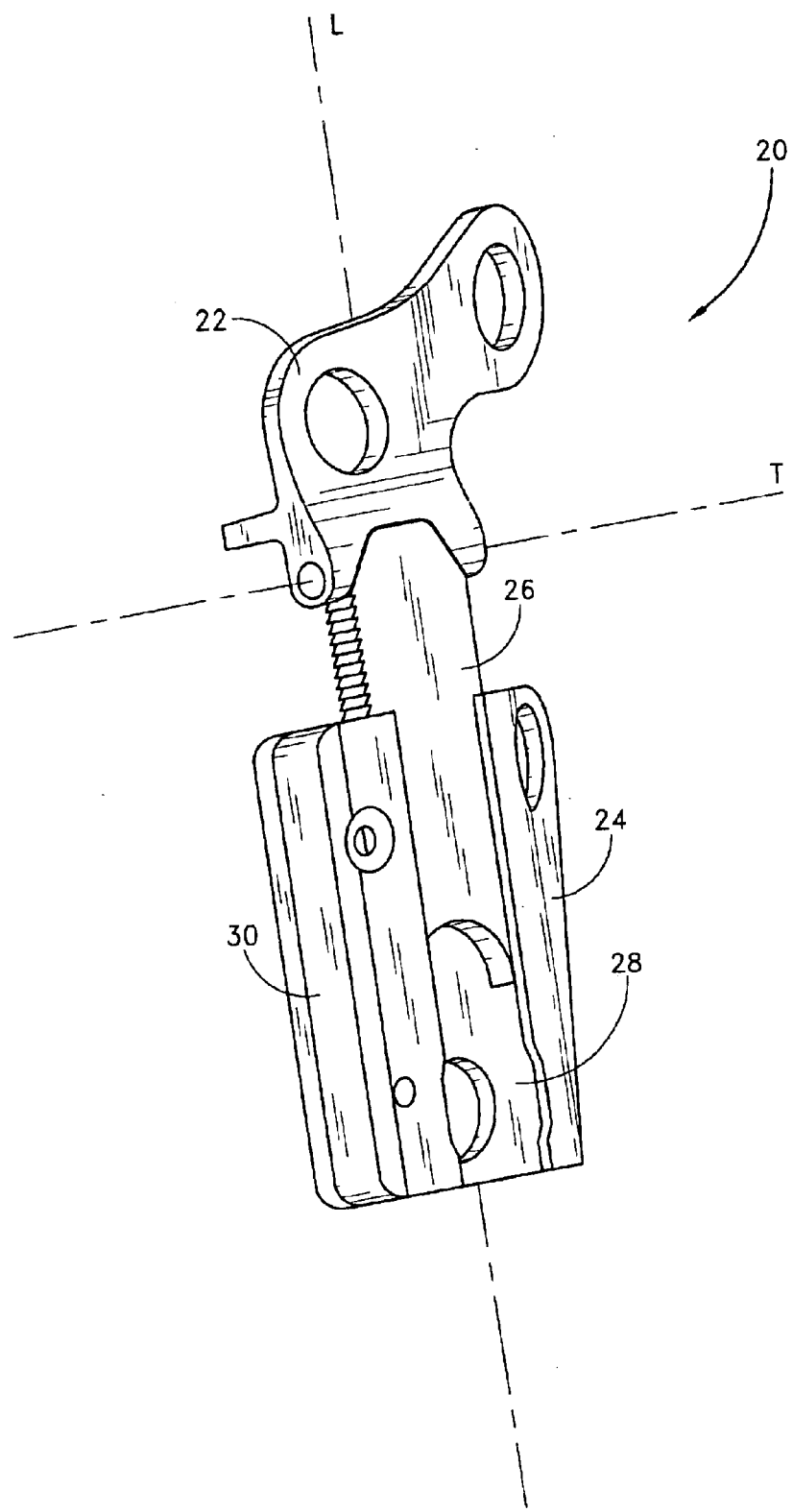
FIG. 1 is a front perspective view of a preferred embodiment of the internal osteotomy fixation device according to the present invention.
Figure 2:
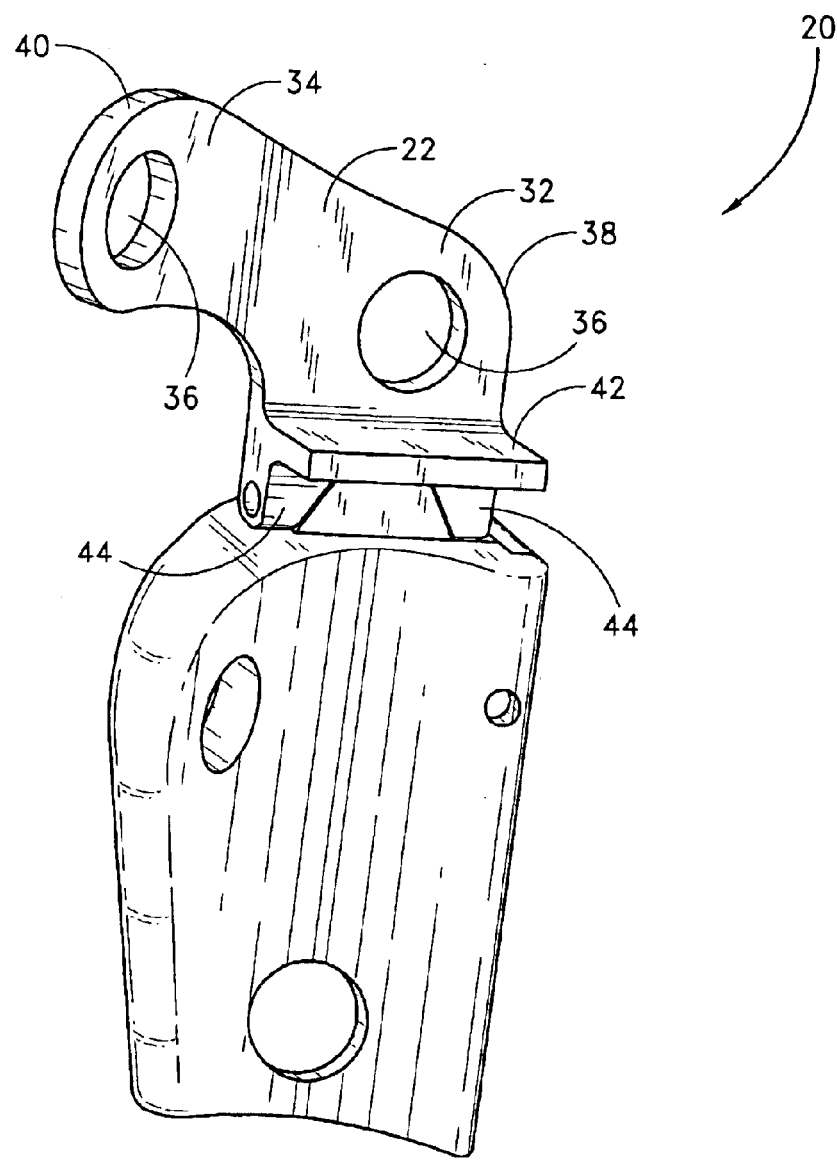
FIG. 2 is a rear perspective view of the internal osteotomy fixation device of FIG. 1.

FIGS. 1 and 2 illustrate a preferred embodiment of the internal osteotomy fixation device 20. The pictured embodiment is preferably used in connection with an opening wedge medial osteotomy on a patient's left tibia. Therefore, all directional terminology used herein is with reference to this procedure. The device 20 is, however, amenable to other procedures, such as an osteotomy on another bone. Directional terminology should, therefore, not be interpreted as limiting.

With reference to FIG. 1, the device 20 comprises a proximal plate 22 and a distal plate 24. The proximal plate 22 is preferably hingedly connected to a slide 26, which is slidably received within a first channel 28 of the distal plate 24. Thus, the proximal plate 22 is translatable along a longitudinal axis L of the device 20, and pivotable about a transverse axis T that is substantially perpendicular to the longitudinal axis L. A ratchet arm 30 secured to the distal plate 24 controls the extension of the proximal plate 22 from the distal plate 24, as described below.

Figure 3C:
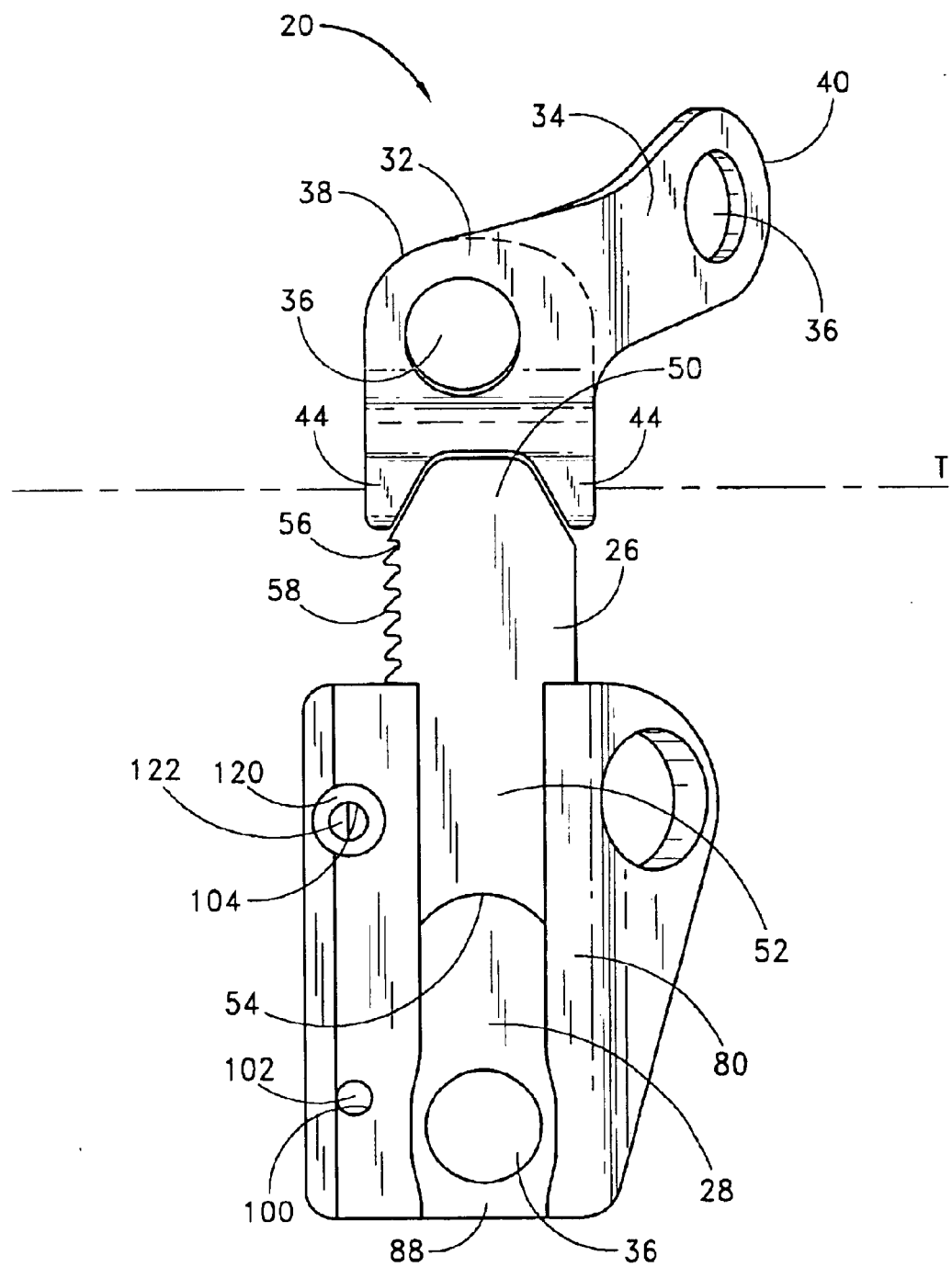
FIG. 3C is a front elevation view of the internal osteotomy fixation device of FIG. 1.

With reference to FIGS. 2, 3A and 3C, the proximal plate 22 includes a first portion 32 and a second portion 34. The first portion 32 is shaped substantially as a half-oval in front elevation aspect (FIG. 3C), and defines a plane that is substantially parallel to a plane defined by the slide 26. The second portion 34 is also shaped substantially as a half-oval, but extends at an angle of approximately 30° away from a plane defined by the first portion 32 (FIG. 3A). The first portion 32 includes a through-hole 36 that is substantially concentric with a curved outer edge 38 of the first portion 32. The second portion 34 includes a through-hole 36 that is substantially concentric with a curved outer edge 40 of the second portion 34. The through-holes 36 are adapted to receive bone screws or other attachment devices, which are used to secure the proximal plate 22 to a patient's bone.

Figure 3D:
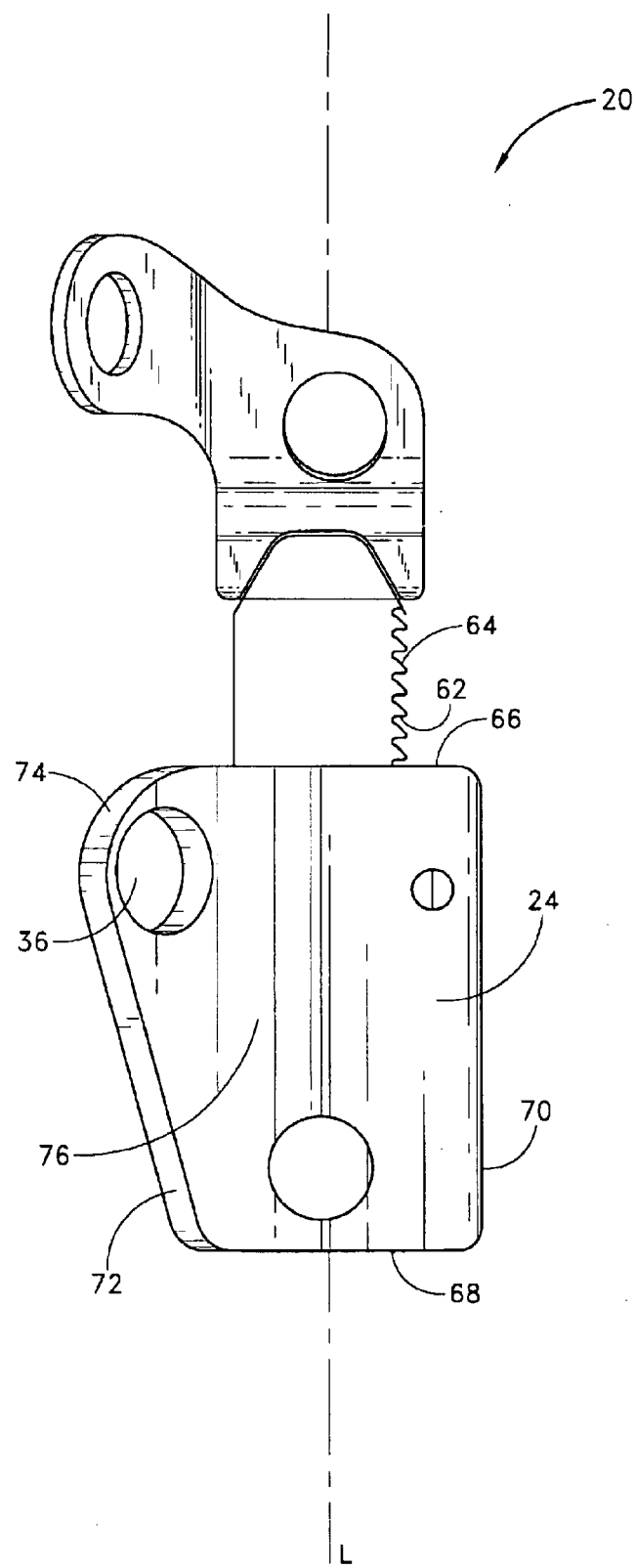
FIG. 3D is a rear elevation view of the internal osteotomy fixation device of FIG. 1.
Figure 3E:
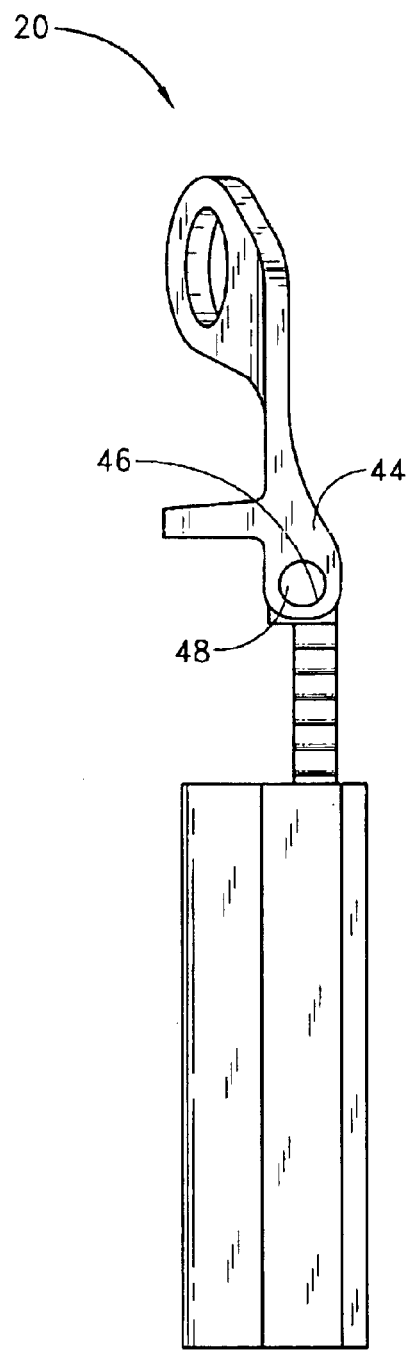
FIG. 3E is a left-side elevation view of the internal osteotomy fixation device of FIG. 1.
Figure 3F:
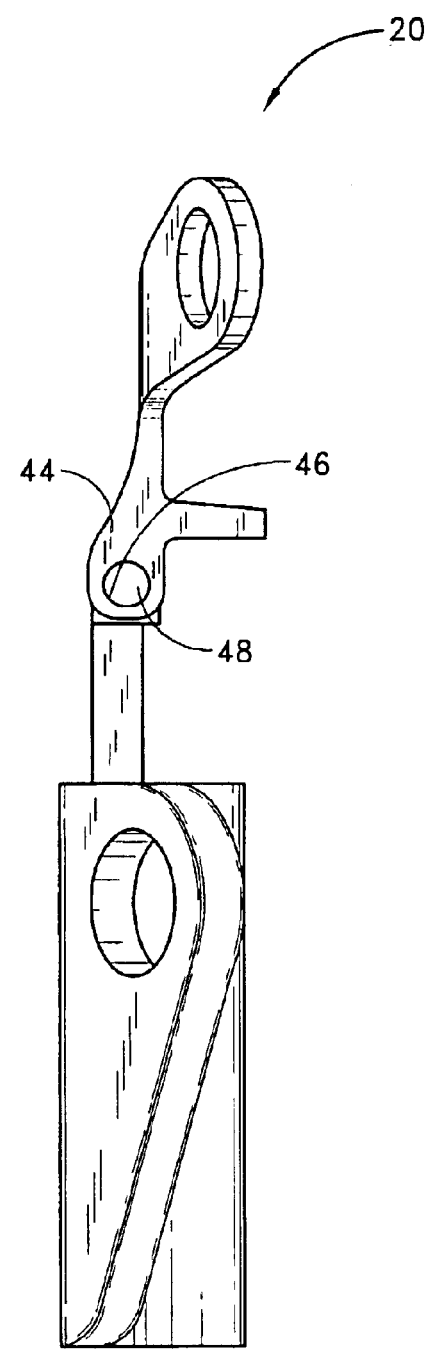
FIG. 3F is a right-side elevation view of the internal osteotomy fixation device of FIG. 1.

A substantially rectangular ledge 42 extends from an edge of the first portion 32 in a direction perpendicular to the first portion 32, to the same side of the first portion 32 as the second portion 34 extends. First and second lugs 44, spaced from one another, extend from the same edge of the first portion 32, in a direction parallel to the first portion 32. With reference to FIGS. 3E and 3F, each of the first and second lugs 44 includes a through-hole 46. Centers of the through-holes 46 define the transverse axis T (FIGS. 1 and 3C).

The lug through-holes 46 receive end portions of a substantially cylindrical hinge pin 48. A transverse slot (not shown) located on a proximal end 50 (FIG. 3C) of the slide 26 receives a central portion of the hinge pin 48. The slot is thus coaxial with the lug through-holes 46 and the transverse axis T. The proximal plate 22 is also thus hingedly connected to the slide 26, and is free to pivot about the axis T.

The slide 26 comprises a substantially rectangular flat plate in front elevation aspect (FIG. 3C). A slide distal end 52 includes a cut-out portion 54, which is preferably semicircular. An edge 56 of the slide 26 includes teeth 58, which cooperate with ratchet teeth 60 on the ratchet arm 30 (FIGS. 5C and 6A) to control the degree of extension of the slide 26 with respect to the distal plate 24, as explained below. In the illustrated embodiment, the edge 56 is a posterior edge of the slide 26. One of skill in the art will appreciate, however, that the teeth 58 could be located, for example, on an anterior edge of the slide 26.

Each slide tooth 58 includes a first face 62 (FIG. 3D) defining a plane that is perpendicular to the longitudinal axis L of the slide 26. The first faces 62 face the distal end 52 (FIG. 3C) of the slide 26. Each slide tooth 58 also includes a second face 64 (FIG. 3D) that intersects both the plane defined by the first face 62, and the longitudinal axis L of the slide 26, at an approximately 45° angle. The second faces 64 face the proximal end 50 (FIG. 3C) of the slide 26.

The distal plate 24 is substantially trapezoidal in rear elevation aspect (FIG. 3D), including two parallel edges 66, 68 that intersect a third edge 70 at two 90° angles, and a fourth straight edge 72 that intersects parallel edge 68 in an obtuse angle, and intersects parallel edge 66 in a radiused corner 74. In the illustrated embodiment, all corners of the distal plate 24 are rounded off to decrease the likelihood that the corners will cause trauma to surrounding tissue after the device 20 is implanted. One of skill in the art will appreciate, however, that the corners could also be unrounded.

Adjacent the radiused corner 74 is a through-hole 36 that is adapted to receive a bone screw or other device for securing the distal plate 24 to a patient's tibia. The distal plate 24 also comprises a bone engaging, or lateral surface 76. The lateral surface 76 defines an arc 78 that lies in a plane perpendicular to the longitudinal axis L of the distal plate 24 (FIG. 3B). The radius of the arc 78 is preferably variable, and adapted to conform to the curvature of a human tibia.

Figure 4A:
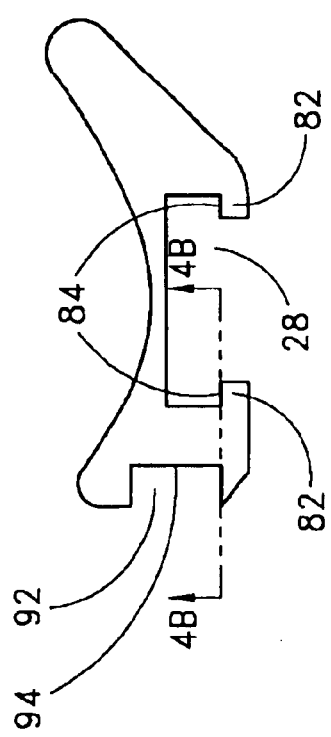
FIG. 4A is a top plan view of the distal plate of the internal osteotomy fixation device of FIG. 1.

The distal plate 24 includes a first longitudinal channel 28 (FIGS. 3C and 4A) in a medial face 80. The first channel 28 is substantially U-shaped in plan aspect, but includes first and second overhanging lips 82 bounding the open end of the U-shape. The first channel 28 is adapted to slidably receive the slide 26. A lateral surface 84 of each lip 82 (FIG. 4A) contacts a medial surface 86 of the slide 26 (FIG. 3B), thereby restraining the slide 26 against movement in a medial direction. A distal portion 88 (FIG. 3C) of the first channel 28 includes a through-hole 36 that is adapted to receive a bone screw or other device 20 for attaching the distal plate 24 to a patient's bone.

The distal plate 24 includes a second channel 92 (FIG. 4A) that is parallel to the first channel 28. In the illustrated embodiment, the second channel 92 is located on a posterior portion 90 of the distal plate 24. One of skill in the art will appreciate, however, that the second channel 92 could be located, for example, on an anterior portion of the distal plate 24.

The second channel 92 is substantially U-shaped in cross-section. A floor 94 (FIG. 4B) of the second channel 92 comprises a contoured surface having varying elevation in the longitudinal direction. The floor 94 terminates a short distance from the edge 66 of the distal plate, and includes a shelf 96, defining a plane substantially perpendicular to the longitudinal axis L.

One of skill in the art will appreciate that the orientation of the various features of the device 20 are easily rearrangeable. For example, in an opening wedge medial osteotomy on a patient's left tibia, the second channel 92 may be located on an anterior portion of the distal plate 24, rather than the posterior portion as illustrated. In such a configuration, the slide ratchet teeth 58 would be located on an anterior surface of the slide 26 to facilitate interaction between the slide ratchet teeth 58 and the ratchet arm ratchet teeth 60. Also, the device 20 may be flipped so that the proximal plate 22 is distal of the distal plate 24, and vice versa. Other reorientations and rearrangements are within the scope of the device 20, and will be apparent to those skilled in the art.

Figure 4B:
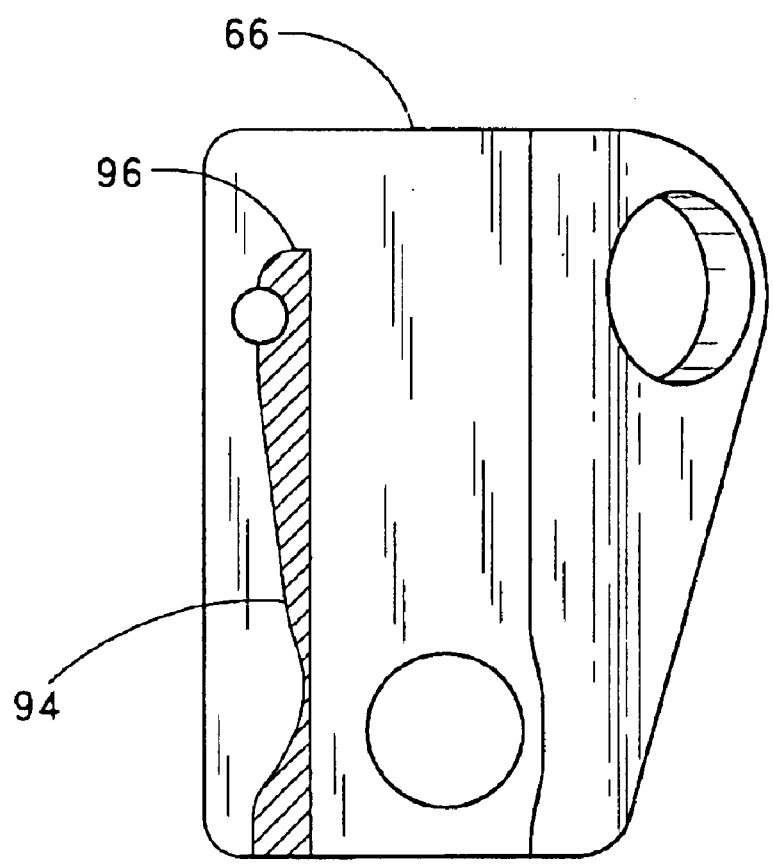
FIG. 4B is a partial section view of the distal plate of FIG. 4A from a front elevation perspective.
Figure 4C:
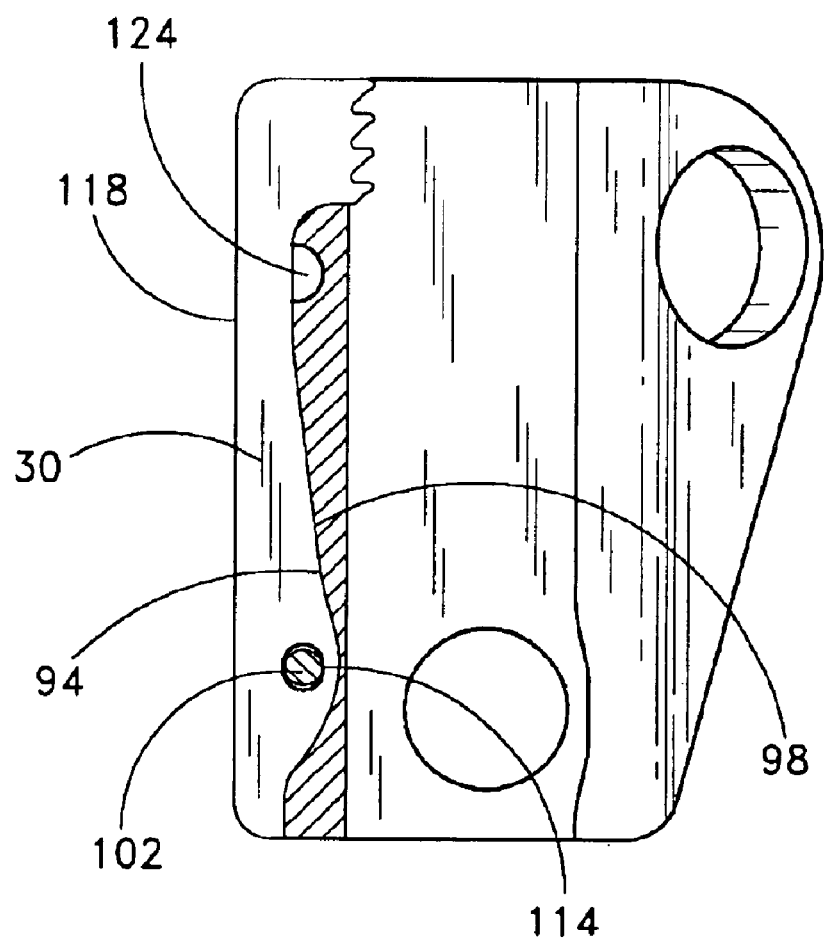
FIG. 4C is a partial section view of the distal plate of FIG. 4A and the ratchet arm from a front elevation perspective.
Figure 12:
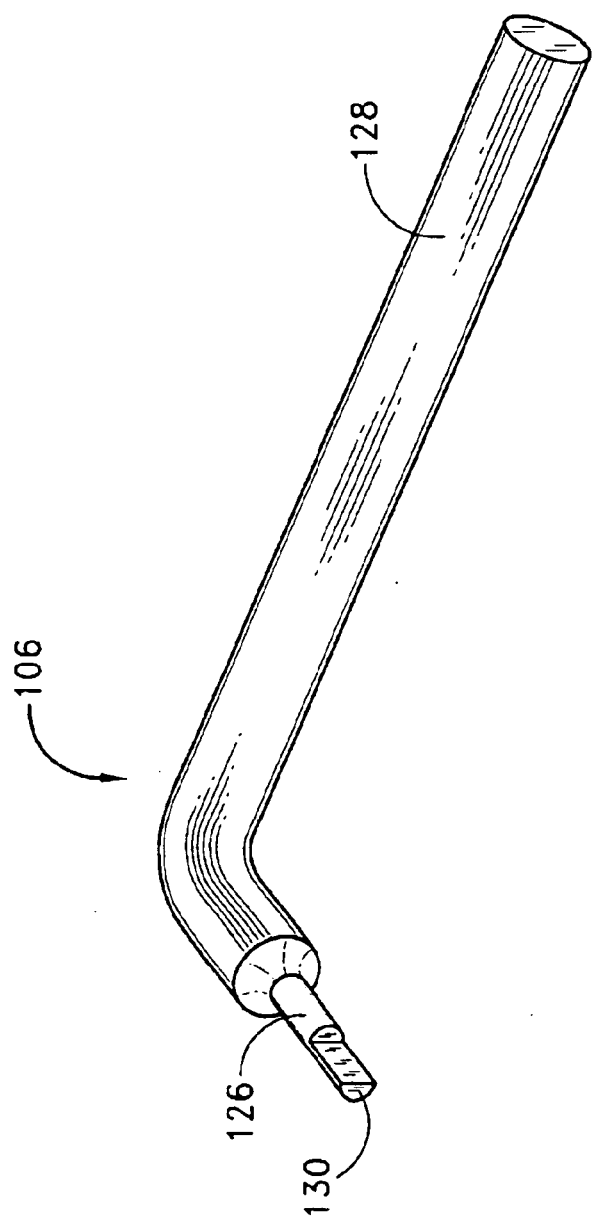
FIG. 12 is a front perspective view of a release tool useful for retracting the internal osteotomy fixation device of FIG. 1 after implantation.

The floor 94 is adapted to receive and mate with a first surface 98 of the ratchet arm 30 (FIG. 6A), which is disposed within the second channel 92 (FIG. 4C). A first through-hole 100 (FIG. 3C) in a sidewall of the second channel receives a pin 102 upon which the ratchet arm 30 is mounted, as explained below. A second through-hole 104 (FIG. 3C) in the sidewall is adapted to receive a release tool 106 (FIG. 12). A physician uses the release tool 106 to disengage the ratchet arm 30 from the slide 26 in order to retract the device 20, as explained below.

The ratchet arm 30, which is disposed within the second channel 92, comprises an elongate arm resembling a toothbrush (FIGS. 6A and 6B). A proximal end 108 of the arm includes a raised portion 110 including a plurality of ratchet teeth 60. The ratchet teeth 60 are substantially identical to the slide teeth 58, however, their orientation is reversed. Thus, teeth faces that are perpendicular to the longitudinal axis L face the ratchet arm proximal end 108, while faces that are oriented at a 45° angle relative to the longitudinal axis L face a distal end 112 of the ratchet arm 30.

The ratchet arm distal end 112 includes a transverse through-hole 114 having a substantially oval shape. The hole 114 is adapted to receive a first end of the cylindrical pin 102 (FIGS. 3C and 4C). The first through-hole 100 in the sidewall of the second channel 92 of the distal plate 24 receives a second end of the pin 102. Preferably, a friction fit retains the pin in the hole 100.

A maximum width of the oval hole 114, measured in a direction parallel to the transverse axis T, is substantially equal to a diameter of the pin 102. A length of the oval hole 114, however, is preferably greater than the diameter of the pin 102. The ratchet arm 30 is thus free to translate a small amount along the longitudinal axis L relative to the pin 102 and the distal plate 24. This configuration prevents the ratchet arm 30 from bearing compressive loads, as explained below.

The first surface 98 of the ratchet arm 30 abuts the second channel floor 94 (FIG. 4C). The ratchet arm first surface 98 is preferably complimentary to the contour of the second channel floor 94. Because the portion of the ratchet arm 30 that is distal of the oval hole 114 directly abuts the second channel floor 94, the ratchet arm 30 is constrained against rotation about the pin 102. Preferably, a second surface 118 (FIG. 6A) of the ratchet arm 30, opposite the first surface 98, is substantially flat.

Locating the ratchet arm 30 on the posterior surface 118 of the device 20 (or the anterior surface, as described above) significantly reduces the dimension of the device 20 that protrudes from the surface of a patient's bone. Thus, the device 20 causes very little deformation of a patient's overlying skin. Such deformation can not only be unsightly, but can cause irritation to the surrounding tissue. Foreign objects placed within the body tend to irritate the body. The larger the object, the more it displaces and deforms the body. Generally, the more an object displaces and deforms the body, the more it causes irritation. Thus, reducing the distance the device 20 protrudes from the bone surface reduces irritation to the tissue surrounding the device 20.

Figure 5A:
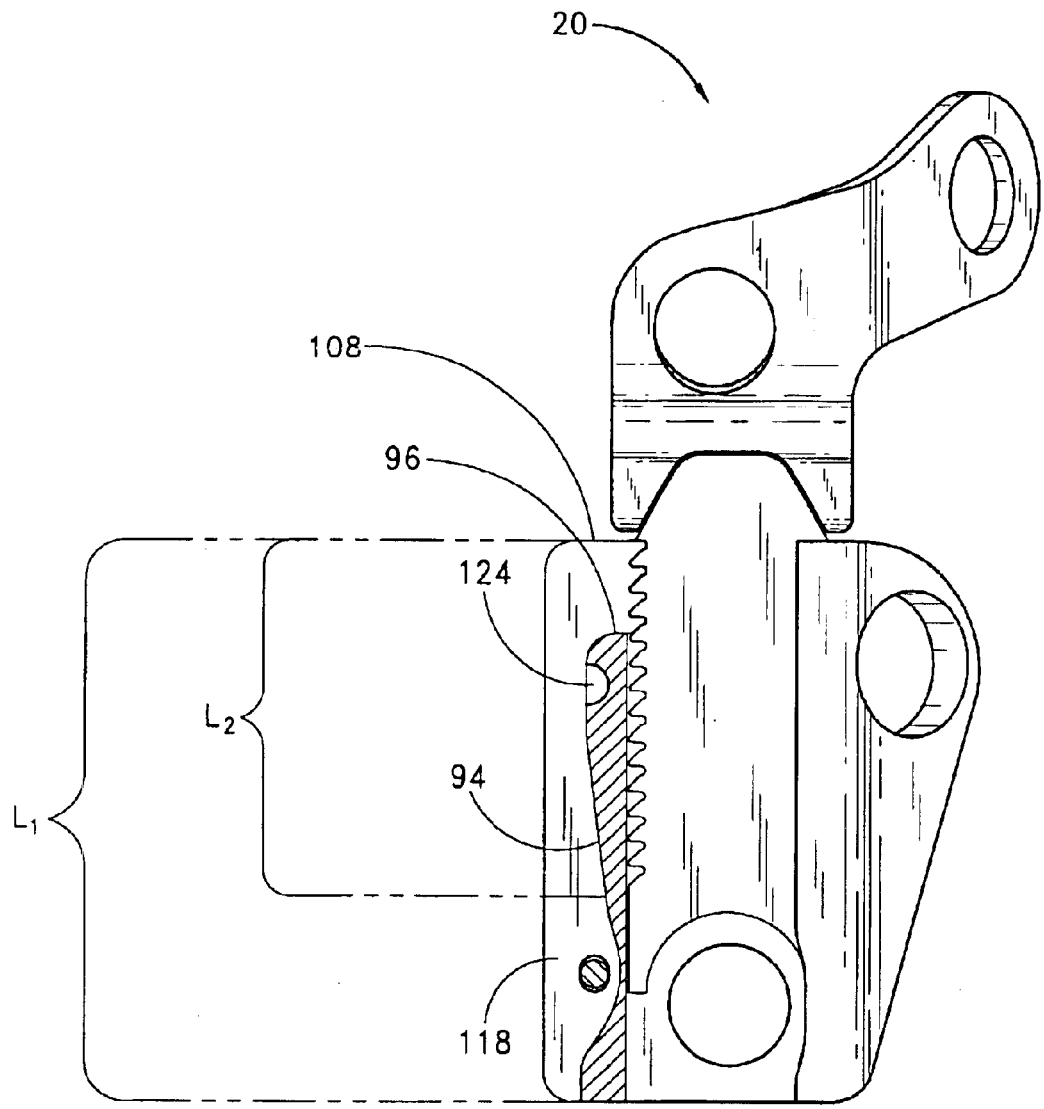
FIG. 5A is a partial section view of the internal osteotomy fixation device of FIG. 1, in the fully retracted position, from a front elevation perspective, illustrating the interconnection of the ratchet arm and the slide.
Figure 5B:
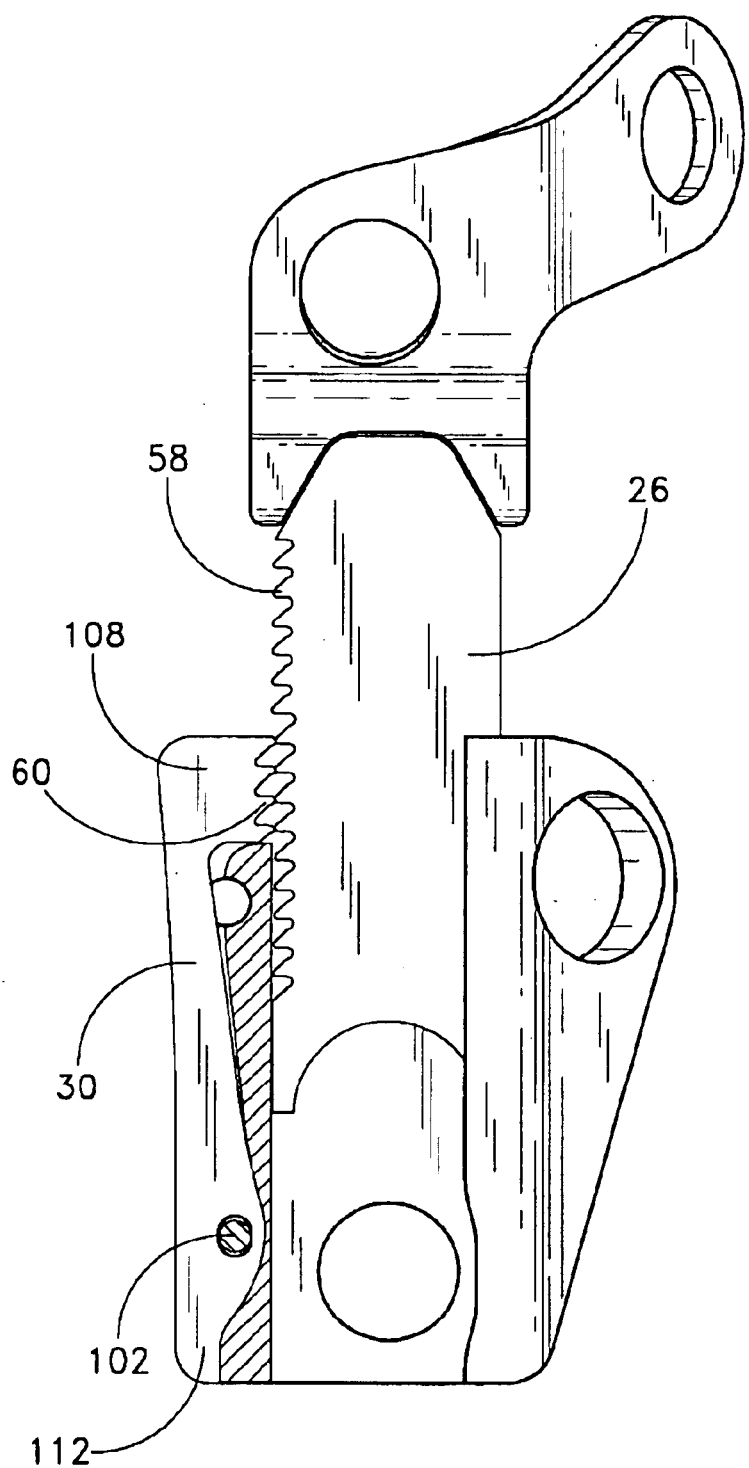
FIG. 5B is a partial section view of the internal osteotomy fixation device of FIG. 1, in a partially retracted position, from a front elevation perspective, illustrating the flexing of the ratchet arm as the slide advances and the device lengthens.
Figure 5C:
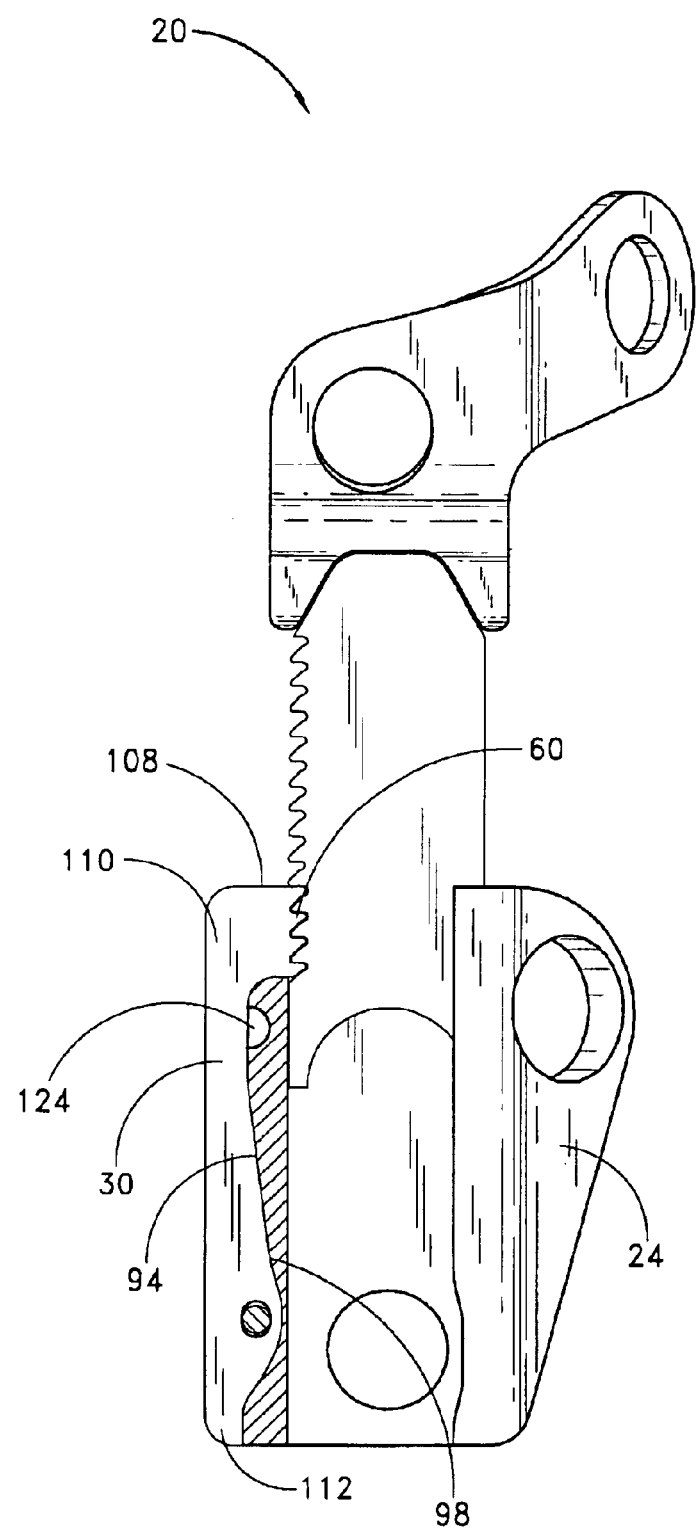
FIG. 5C is a partial section view of the internal osteotomy fixation device of FIG. 1, in the fully extended position, from a front elevation perspective, illustrating the interconnection of the ratchet arm and the slide.

FIG. 5A depicts the device 20 in its fully retracted configuration, while FIG. 5C depicts the device 20 in its fully extended configuration. From the fully retracted configuration, an applied tensile force parallel to the longitudinal axis L causes the sloped teeth faces 64 (FIG. 3D) on the slide 26 to bear against the sloped teeth faces on the ratchet arm 30. The resultant force from this interference tends to push the ratchet arm proximal end 108 away from the slide 26. Because the ratchet arm distal end 112 is constrained against rotation about the pin 102, the ratchet arm flexes like a cantilevered beam along its length between the pin 102 and the proximal end 108 (FIG. 5B). The ratchet teeth 60 thus move laterally away from the slide teeth 58 a sufficient amount to allow the slide 26 to pass. After the slide teeth 58 move one notch relative to the ratchet teeth 60, the strain in the flexed arm 30 relaxes, causing the ratchet arm 30 to snap back to the unflexed configuration as in FIGS. 5A and 5C.

As FIG. 6A shows, the cross-sectional area of the ratchet arm 30 decreases from the region near the oval hole 114 toward the region near the raised portion 110. When the ratchet arm 30 flexes (FIG. 5B), this configuration maintains a constant stress level along the flexed portion of the ratchet arm 30. The lack of stress concentrations maximizes the flexibility per unit length of the ratchet arm 30.

Figure 7A:
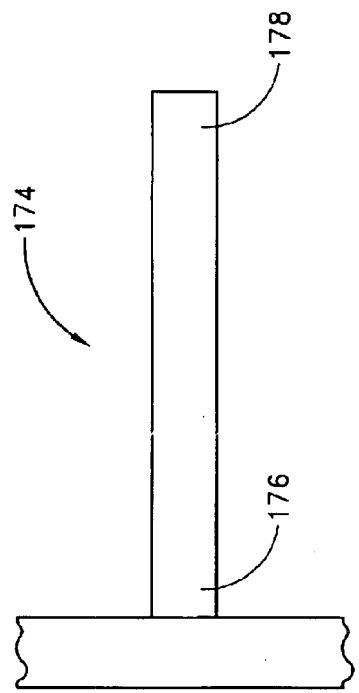
FIG. 7A is a schematic view of an unloaded cantilevered beam having a variable cross-section.
Figure 7B:
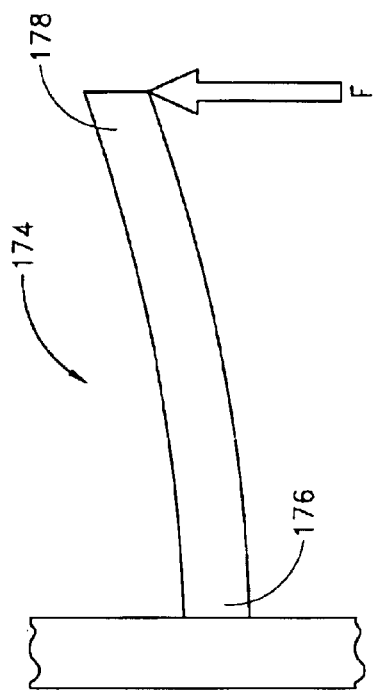
FIG. 7B is a schematic view of an unloaded cantilevered beam having a constant cross-section.
Figure 7C:
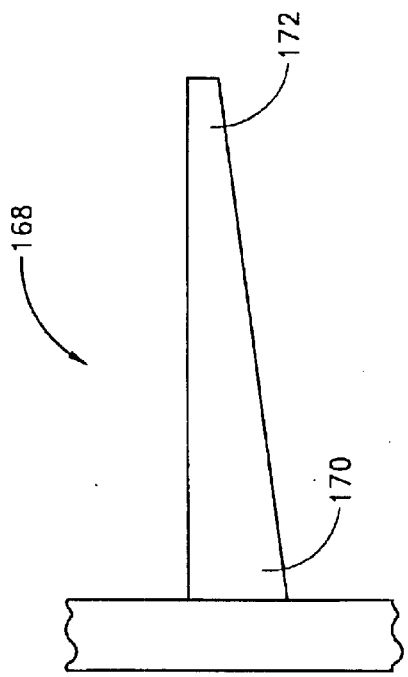
FIG. 7C is a schematic view of the cantilevered beam of FIG. 7A having a vertical load applied.
Figure 7D:
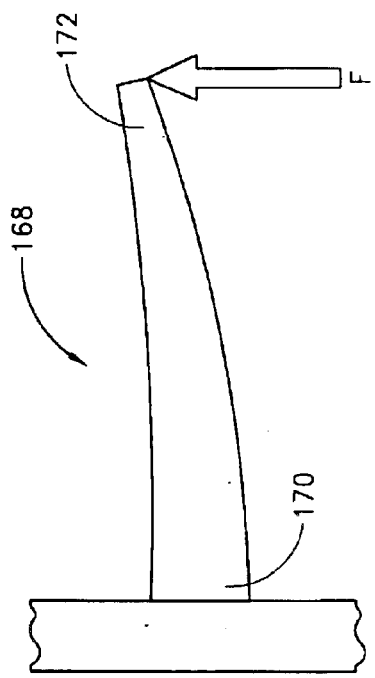
FIG. 7D is a schematic view of the cantilevered beam of FIG. 7B having a vertical load applied.

This principle is illustrated in FIGS. 7A–7D. FIG. 7A depicts a cantilevered beam 168 having a cross-sectional area that gradually decreases from a fixed base portion 170 toward a free end portion 172. The varying cross-section of the beam 168 represents the varying cross-section of the ratchet arm 30. FIG. 7B depicts a cantilevered beam 174 having a constant cross-sectional area from a fixed base portion 176 toward a free end portion 178. In FIGS. 7C and 7D, each beam 168, 174 is subjected to a simple point load F that is perpendicular to a longitudinal axis of each beam 168, 174. The load F represents the force exerted on the ratchet arm 30 by the slide teeth 58 as the slide 26 moves relative to the ratchet arm 30 (FIG. 5B). The load F causes each beam 168, 174 to flex.

The stress at any point in either beam 168, 174 is directly proportional to the distance between that point and the load F, and inversely proportional to the beam cross-sectional area. Thus, the stress in the beam 168 is relatively constant along the beam's length as compared to the stress in the beam 174. In the beam 174 stress increases with distance from the load F, because the cross-sectional area of the beam 174 is constant. In the beam 168, by contrast, stress may increase with distance from the load F, but the increasing cross-sectional area from the end portion 172 toward the base portion 170 tempers this increase, and in fact may cause the stress in the beam 168 to decrease towards the base portion 170, depending upon the beam dimensions.

The constant stress level along the length of the variable cross-section beam 168 increases the flexibility of the beam 168. With the constant cross-section beam 174, stress concentrations develop in the base portion 176 with applied loads. Stress concentrations lead to failure. With the variable cross-section beam 168, however, no stress concentrations develop along the beam 168, and the free end 172 may be displaced a greater amount before the beam 168 fails.

Flexibility is an important characteristic of the ratchet arm 30. First, the more flexible the ratchet arm 30 is, the less likely it is to fail. Second, the tensile force necessary to extend the device 20 is preferably above a certain minimum to prevent inadvertent extension of the device if the patient falls down, for example. However, the tensile force necessary to extend the device 20 is also preferably below a certain maximum so as to minimize patient discomfort during the extension procedure, which is described below. Third, the device 20 is desirably as small as possible to minimize irritation to the patient's surrounding tissue. Therefore, the ratchet arm 30 is also desirably as small as possible. However, ratchet arm flexibility generally decreases proportionately with ratchet arm length, because the bending moment generated by the applied tensile force is proportional to ratchet arm length. By maximizing the flexibility per unit length of the ratchet arm 30, the device 20 may be provided with a shorter ratchet arm than would be possible if a ratchet arm having a constant cross-section were provided. The unique shape of the ratchet arm 30 thus decreases the overall device dimensions.

Referring to FIG. 3C, the distal plate 24 includes a circular through-hole, or release mechanism access hole 104. Part of the hole 104 extends through the second channel 92, and part of the hole 104 extends through the second channel floor 94, as FIG. 4B illustrates. The distal plate medial surface 80 includes a circular beveled portion 120 surrounding a medial extent of the hole 104 (FIG. 3C). The position of the ratchet arm 30 within the second channel 92 is such that a portion 122 of the ratchet arm 30 blocks a portion of the hole 104 (FIG. 3C). As FIGS. 4C, 5A and 5C illustrate, the portion 122 creates a semi-circular gap 124 between the ratchet arm first surface 98 and the second channel floor 94. A portion of a release tool 106, pictured in FIG. 12, is insertable within the gap 124.

The release tool 106 comprises a head 126 mounted on a generally L-shaped handle 128. The head 126 is shaped as a cylinder having a half-cylindrical section removed from a portion distal of the handle 128. The distal extent 130 of the head 126 thus has a semi-circular cross-section that is dimensioned to fit snugly within the semi-circular gap 124 in the release mechanism access hole 104. Rotating the head 126 within the gap 124 forces the ratchet arm 30 to flex, and moves the ratchet teeth 60 laterally away from the slide teeth 58. With the ratchet teeth 60 disengaged from the slide teeth 58, the slide 26 and the proximal plate 22 are freely translatable with respect to the distal plate 24, and the device 20 may be contracted by applying a compressive force along the longitudinal axis L. Advantageously, the physician may contract the device 20 in this manner during the implantation procedure. The device 20 may thus be adjusted to the optimum length prior to closing the patient's incision.

Figure 8:
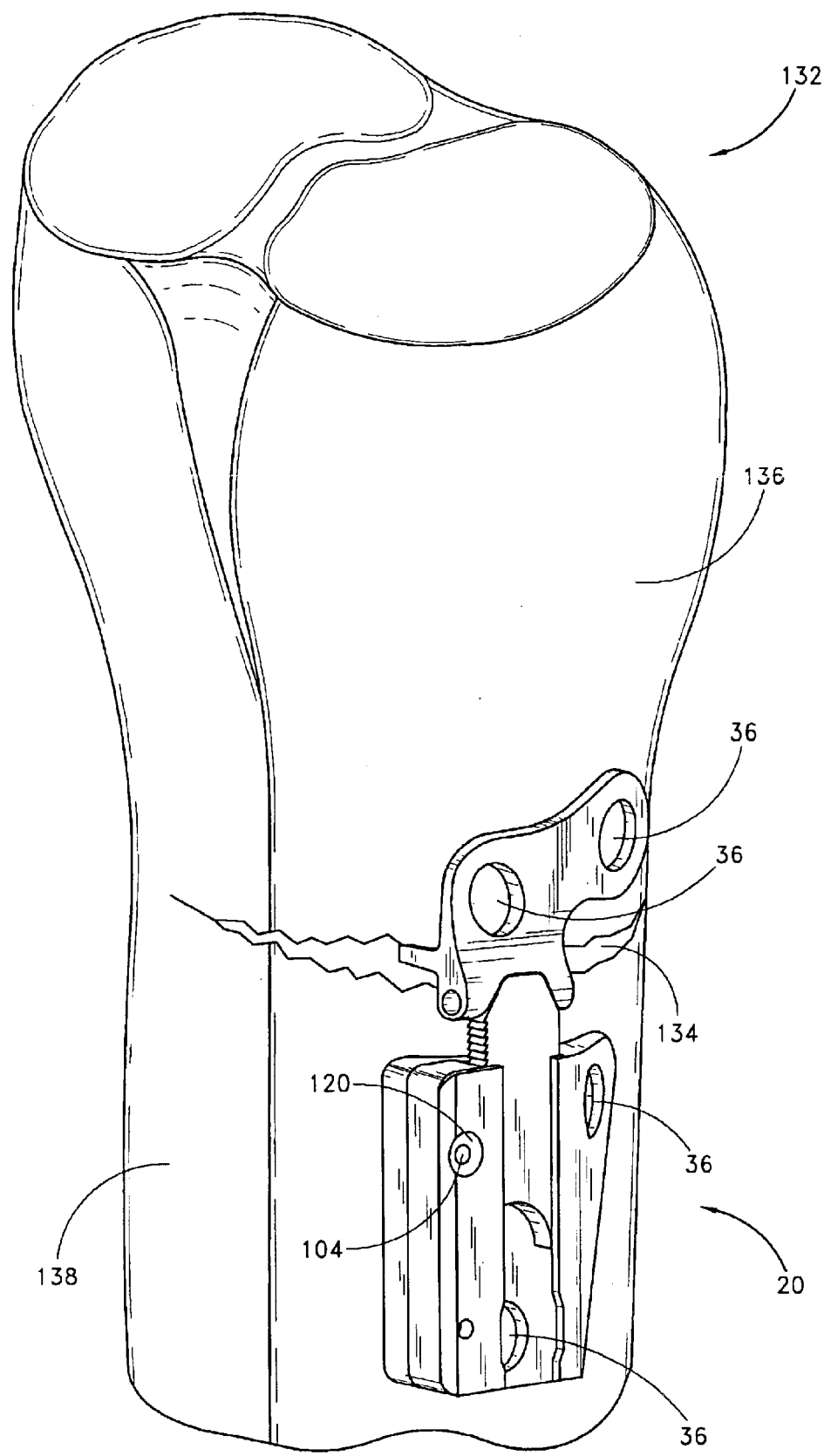
FIG. 8 is a front perspective view of the internal osteotomy fixation device of FIG. 1 implanted on a medial side of a human tibia.
Figure 9A:
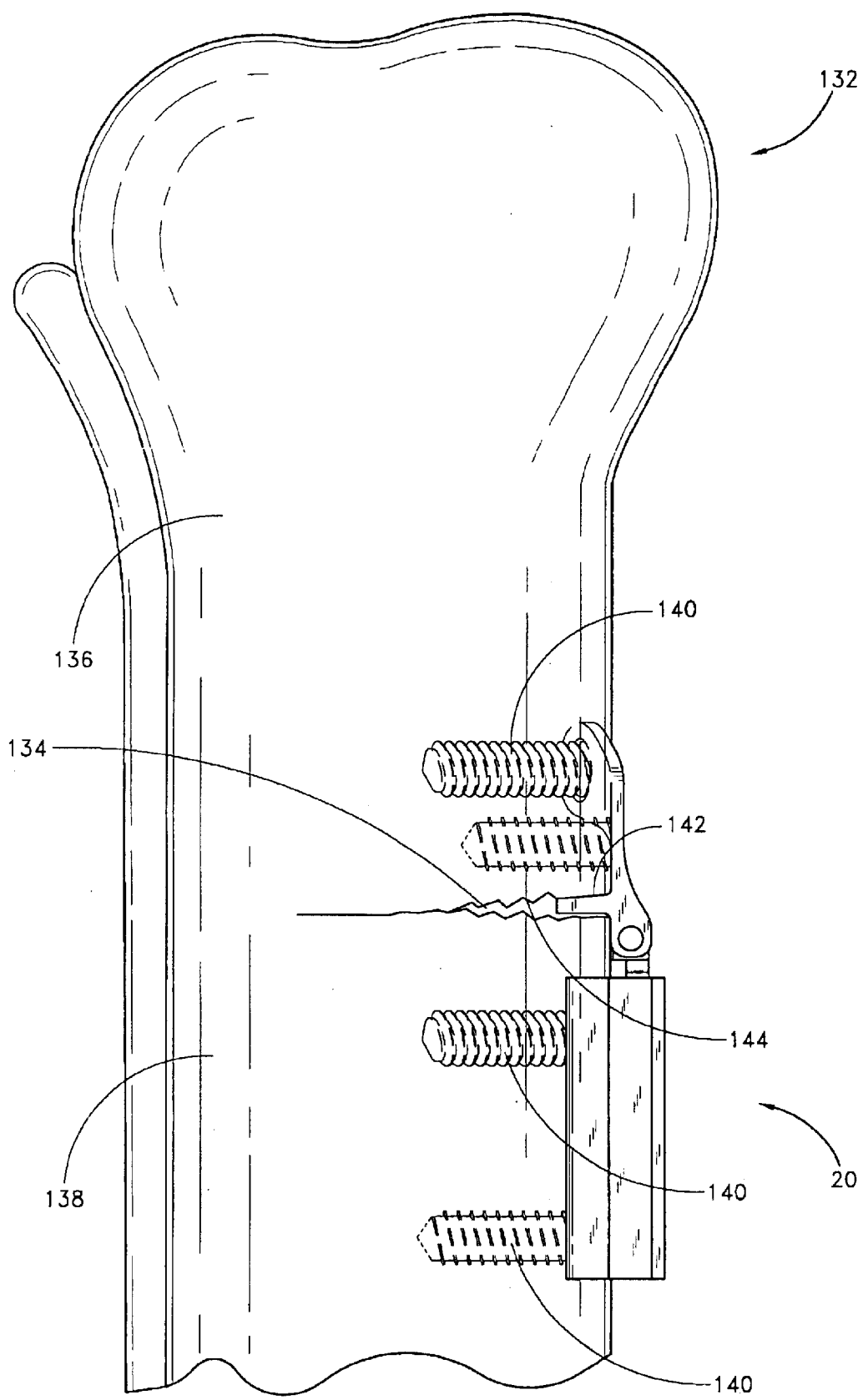
FIG. 9A is a posterior view of the internal osteotomy fixation device of FIG. 1, illustrating the configuration of the device and bone immediately after implantation.
Figure 9B:
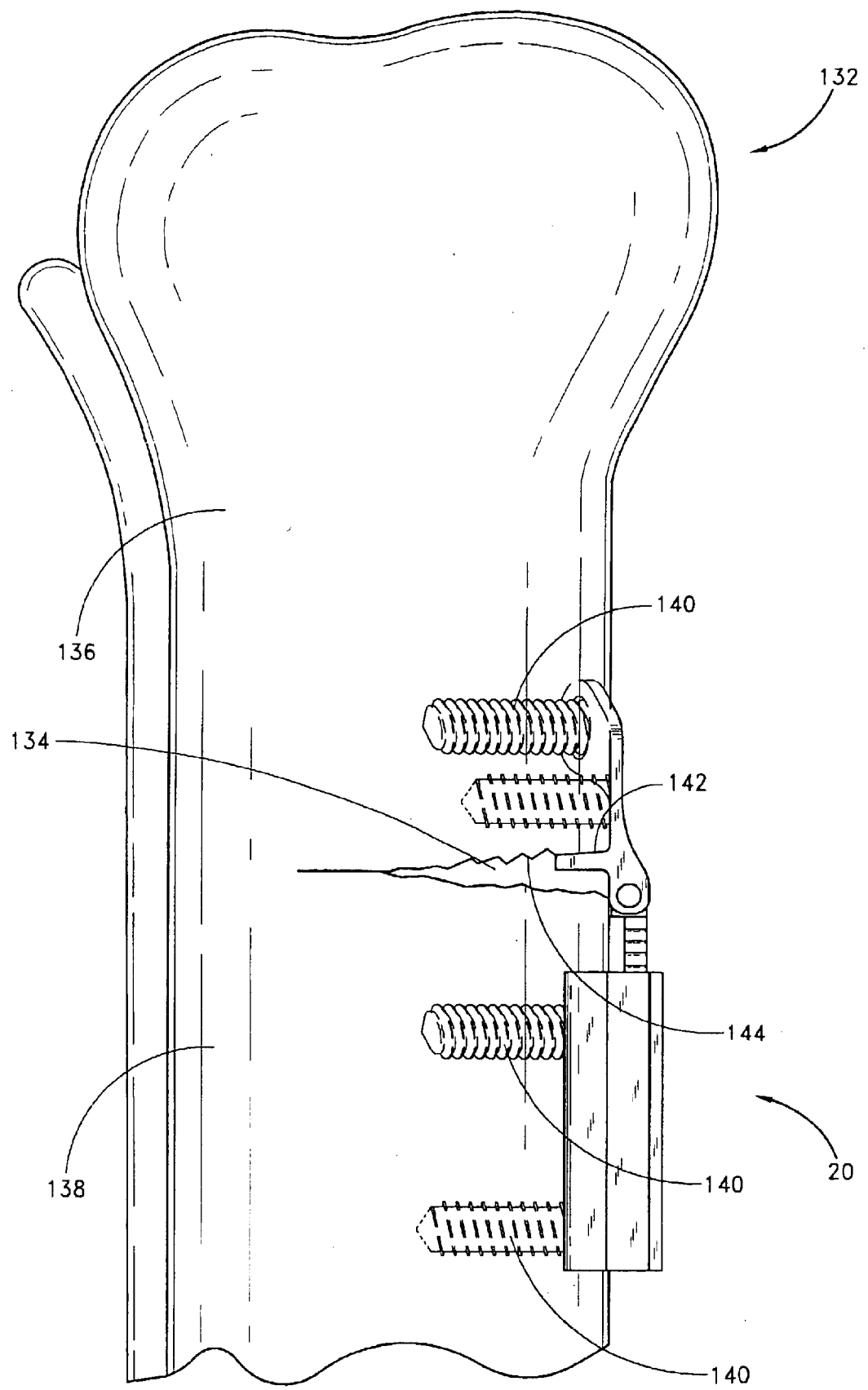
FIG. 9B is a posterior view of the internal osteotomy fixation device of FIG. 1, illustrating the configuration of the device and bone after some distraction of the tibial incision.

FIG. 8 illustrates the device 20 and a tibia 132 in a post-operative configuration for a high-tibial medial opening wedge osteotomy. The physician has made a transverse cut 134 in the patient's tibia 132 from the medial side. Although the cut 134 does not completely sever the tibia 132, it effectively divides the tibia 132 into a proximal segment 136 and a distal segment 138. The device 20 is secured to the medial side of the tibia 132, with the proximal plate 22 attached to the proximal segment 136, and the distal plate 24 attached to the distal segment 138. In FIGS. 9A and 9B, bone screws 140 extend through through-holes 36 into the tibia 132 to fasten the device 20 in place. One of skill in the art will appreciate, however, that other fastening devices, such as spikes, may be used in place of bone screws 140. Preferably, a proximal surface 142 of the ledge 42 contacts a distal surface 144 of the proximal bone segment 136. The ledge 42 supports the proximal bone segment 136, relieving some stress that would otherwise be borne by the screws 140. The ledge 42 thus reduces the trauma to the proximal bone segment 136, and reduces the likelihood that one or more of the screws 140 will pull out, causing the proximal plate 22 to become disengaged from the proximal bone segment 136.

FIG. 9A illustrates the device 20 shortly after implantation on the medial surface of the patient's tibia 132, when the device 20 is used to perform an opening wedge osteotomy according to one preferred method. The device 20 is in its fully retracted configuration, and the tibial incision 134 is only slightly distracted. In a preferred embodiment, after the implantation procedure the incision 134 is allowed to heal for a few days. During this time, the severed surfaces of the incision 134 begin to reattach to one another by growing new bone tissue. The new bone tissue is spongy and flexible. Therefore, when the tibial incision 134 is distracted, as shown in FIG. 9B, the new bone tissue stretches. After stretching, the incision 134 is again allowed to heal for a few days to a few weeks. During this time, more bone tissue grows to fill the wider gap between the tibial segments. After healing, the incision 134 is again distracted, stretching the new spongy bone growth. This incremental stretching and healing is repeated until the width of the gap becomes sufficient to properly align the patient's joint. For example, the physician may adjust the patient's leg one to seven degrees per week. One of skill in the art will appreciate, however, that many rates of adjustment are possible, and that the rate of adjustment should be determined according to the patient's needs. Gradually, the spongy bone tissue calcifies and the incision 134 heals completely.

In a preferred embodiment in which the osteotomy fixation device 20 is especially adapted to be fit to a human tibia, the physician may use an external extension brace 146 like the one pictured in FIGS. 10A and 10B to distract the tibial incision 134. The brace 146 has a generally flat surface 148 upon which the patient places his or her leg 150. The brace 146 includes a first pad 152 positioned to provide a first contact point with the medial side 154 of the femoral portion of the patient's leg 150. The brace 146 further includes a second pad 156 positioned to provide a second contact point with the medial side 154 of the tibial portion of the patient's leg 150, distal to the device 20. In a preferred embodiment, the first pad 152 and second pad 156 are fixed.

The external brace 146 further includes a third pad 158 positioned to provide a third contact point with the lateral side 160 of the tibial portion of the patient's leg 150. The third contact point is preferably directly opposite the device 20. The third pad 158 is laterally adjustable. In one preferred embodiment, the third pad 158 includes a fixed plate 162 having an internally threaded opening therein. A lead screw 164 is disposed within the opening. A first end of the lead screw 164 is attached to the pad 158. A handle 166 is attached to the second end of the lead screw 164. Rotation of the handle 166 in a first direction advances the lead screw 164, and thus the pad 158, in the medial direction. Rotation of the handle 166 in the opposite direction advances the lead screw 164, and thus the pad 158, in the lateral direction.

Movement of the third pad 158 in the medial direction applies a three-point bending load to the patient's leg 150. The lateral side 160 of the leg 150 is in compression, while the medial side 154 is in tension. The tension widens the tibial incision 134. Because the proximal plate 22 is attached to the proximal tibial segment 136, and the distal plate 24 is attached to the distal tibial segment 138, the widening of the tibial incision 134 places the device 20 in tension. The interaction of the ratchet teeth 60 and the slide teeth 58 allows the device 20 to lengthen incrementally, but not retract.

One of skill in the art will appreciate that a variety of configurations and methods may be used to lengthen the device 20. For example, a brace similar to the brace 146 pictured in FIGS. 10A and 10B, but providing a four-point bending load, may be used. In another example, another brace similar to the brace 146 is used, but the third pad 158 and lead screw 164 are replaced by a strap that wraps around the lateral side 160 of the patient's leg 150 opposite the device 20. By pulling on the strap from the medial side 154, the physician applies a force to the lateral side 160 of the patient's leg 150 in the medial direction. This force, together with the forces applied by the first pad 152 and second pad 156, produces a three point bending load that has the same effect as the three point bending load of the brace 146.

Figure 11:
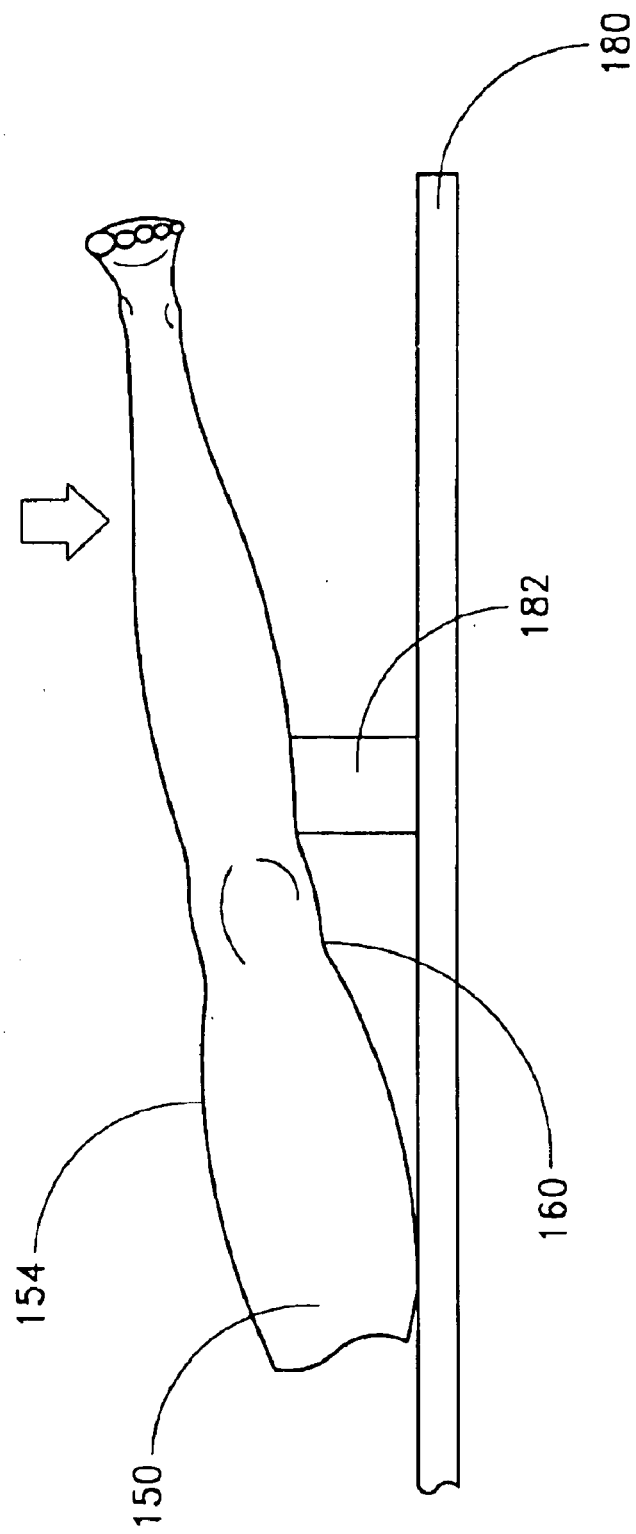
FIG. 11 is a front elevation view of an alternative configuration and method for extending the internal osteotomy fixation device of FIG. 1.

Another example of an alternative method is pictured in FIG. 11. In this configuration, the patient lies on his or her side on a firm surface such as a table 180. A shim 182 is positioned beneath the patient's leg 150, on the lateral side 160, preferably directly opposite the device 20. To lengthen the device, the physician applies downward pressure to the medial side 154 of the patient's leg 150 distal to the device 20, as the arrow in FIG. 11 indicates. This configuration provides a three point bending load, with the patient's weight providing a force in the lateral direction proximal to the device 20, the physician's pressure providing a force in the lateral direction distal to the device 20, and the shim 182 providing a force in the medial direction opposite the device 20.

In another preferred method of using the device 20 to perform an opening wedge osteotomy, the physician determines before or during the implantation procedure how wide the opening wedge should be. He then adjusts the device 20 to the appropriate length and implants it. Generally, if the wedge to be opened is rather wide, the physician packs bone chips or bone graft into the wedge during the implantation procedure. Preferably, no post-implantation adjustment of the device 20 is necessary. In this method, the device 20 performs as a "one-size-fits-all" bone plate. Advantageously, hospitals need not keep a supply of differently sized bone plates on hand, because a supply of the device 20 can be used in a wide variety of different applications.

Under certain circumstances the physician may need to retract the device 20 during or after the implantation procedure. For example, during the implantation procedure the physician may retract the device to arrive at the optimum implantation length, as described above. Alternatively, the physician may need to retract the device after the implantation procedure is complete and the patient's incision has been closed. To do so, the physician makes a very small incision in the patient's skin directly over the location of the release mechanism access hole 104 (FIG. 8). He then inserts the distal end 130 of the head 126 of the release tool 106 (FIG. 12) through the incision and into the semi-circular gap 124 (FIG. 4C). The beveled portion 120 (FIG. 8) of the distal plate 24 guides the release tool distal end 130 into the gap 124 so that the physician need not know the exact location of the gap 124 before inserting the distal end 130. Once the physician has inserted the distal end 130 into the gap 124, he rotates the release tool 106 and disengages the ratchet arm 30 from the slide 26, enabling the device 20 to be retracted in the manner described above.

When the release tool distal end 130 is turned within the gap 124, the lower surface 98 (FIG. 4C) of the flexed ratchet arm 30 pinches the tool distal end 130 against the floor 94 of the second channel 92. Advantageously, once the physician rotates the release tool 106 past 90°, the friction generated by the pinching is sufficient to prevent the release tool 106 from rotating when the physician lets go of the release tool 106. Thus, the physician need not maintain one hand on the release tool 106 while manipulating the extension of the device 20 with the other hand.

In addition to the advantageous features of the device 20 outlined above, several other features make the device 20 particularly well-suited for use in an opening wedge osteotomy of the type just described. First, the proximal plate 22 has two degrees of freedom with respect to the distal plate 24. The proximal plate 22 is translatable along the longitudinal axis L, and rotatable about the transverse axis T (FIG. 1). The device 20 is thus able to conform to the geometry of an opening wedge osteotomy. As the wedge opens (FIG. 9B), not only does the proximal bone segment 136 move longitudinally away from the distal bone segment 138, but the angular alignment of the segments also changes.

If the proximal plate 22 and distal plate 24 could only move longitudinally with respect to one another, as in prior art devices, the motion of the device would not be compatible with the motion of the wedge. As the bone segments tended to change their angular alignment, the unbending device would tend to prevent such adjustment. The competing motions of the wedge and the device would create stresses in the bone and the device. Such stresses would lead to incorrect angular adjustment of the bone segments, and possible disengagement of the device from the bone.

The hinged connection between the proximal plate 22 and slide 26 allows the motion of the device 20 to conform to the motion of the opening wedge. Thus, both the proximal plate 22 and distal plate 24 remain in firm contact with their respective bone segments without creating stresses in the bone. Further, the hinge imparts greater flexibility to the device 20, making it easier to fit the device 20 to bones of different shapes and sizes when initially implanting the device 20.

Second, the relative orientation of the ratchet arm 30 and slide 26 reduces the minimum length of the device 20. As discussed above, the device 20 is advantageously as compact as possible. The minimum length of a linear ratchet mechanism is related to the length $L_1$ of the ratchet arm, and the length $L_2$ of the segment of ratchet teeth that the ratchet arm engages (FIG. 5A). For the device 20, $L_2$ is equal to the length of the segment of slide teeth 58.

In the fully retracted configuration (FIG. 5A), the proximal end 108 of the ratchet arm 30 lines up with the proximal end of the slide teeth 58, and the ratchet arm 30 overlaps the slide teeth 58. The minimum device length is thus dependent upon the longer of $L_1$ or $L_2$, which is the shortest configuration possible. This compact size not only avoids the displacement and deformation problems outlined above, but it also enables the device 20 to be installed through a smaller incision. Thus, the implantation procedure causes less trauma to the patient's surrounding healthy tissue.

Third, the ratchet arm 30 never supports compressive loads. When the device 20 is subjected to a compressive load, the cylindrical pin 102 in the oval hole 114 allows the ratchet arm 30 to slide downward so that the raised portion 110 of the ratchet arm 30 seats down against the shelf 96 (FIG. 5C). The ratchet arm 30 thus transfers compressive forces parallel to the longitudinal axis L directly to the distal plate 24. Because the ratchet arm 30 is not subjected to compressive loads that could cause it to buckle, it may be very thin. The more thin the ratchet arm 30 is, the more flexible it is, and the shorter it may be while still maintaining its flexibility. The combination of shortness and flexibility imparts the device 20 with the beneficial characteristics outlined above.

SCOPE OF THE INVENTION

The above presents a description of the best mode contemplated for the present internal osteotomy fixation device, and of the manner and process of making and using it, in such full, clear, concise, and exact terms as to enable any person skilled in the art to which it pertains to make and use this internal osteotomy fixation device. This internal osteotomy fixation device is, however, susceptible to modifications and alternate constructions from that discussed above which are fully equivalent. Consequently, it is not the intention to limit this internal osteotomy fixation device to the particular embodiments disclosed. On the contrary, the intention is to cover all modifications and alternate constructions coming within the spirit and scope of the internal osteotomy fixation device as generally expressed by the following claims, which particularly point out and distinctly claim the subject matter of the internal osteotomy fixation device.

What is claimed is:

1. An internal osteotomy fixation device, comprising:
   a distal plate including a channel;
   a slide slidably received within the channel such that the slide is translatable with respect to the distal plate along a first axis, the slide having ratchet teeth on a first surface; and
   a ratchet arm fixed to the distal plate, the ratchet arm including teeth configured to engage the slide ratchet teeth;
   wherein the slide includes a first portion defining a first plane, and a ledge defining a second plane substantially perpendicular to the first plane.

2. The internal osteotomy fixation device of claim 1, wherein a proximal surface of the ledge abuts a distal surface of a proximal bone segment when the device is implanted within a patient.

3. An internal osteotomy fixation device, comprising:
   a distal plate including a channel;
   a slide slidably received within the channel such that the slide is translatable with respect to the distal plate along a first axis, the slide having ratchet teeth on a first surface; and
   a ratchet arm fixed to the distal plate, the ratchet arm including teeth configured to engage the slide ratchet teeth;
   wherein a cross-sectional area of the ratchet arm decreases from a distal end of the ratchet arm toward a proximal end of the ratchet arm.

4. The internal osteotomy fixation device of claim 3, wherein the ratchet arm is configured to maintain a constant stress level along a flexed portion of the ratchet arm.

5. The internal osteotomy fixation device of claim 3, wherein the ratchet arm is fixed to the distal plate in a cantilevered fashion.

6. The internal osteotomy fixation device of claim 3, further comprising a proximal plate.

7. The internal osteotomy fixation device of claim 6, wherein the proximal plate is hingedly connected to the slide.

8. An internal osteotomy fixation device, comprising:
   a distal plate including a channel;
   a slide slidably received within the channel such that the slide is translatable with respect to the distal plate along a first axis, the slide having ratchet teeth on a first surface; and
   a ratchet arm fixed to the distal plate, the ratchet arm including teeth configured to engage the slide ratchet teeth;
   wherein the distal plate includes a first surface comprising a shelf, the shelf facing a proximal end of the device; and
   the ratchet arm includes a second surface, the second surface facing a distal end of the device, and the second surface abuts the shelf.

9. The internal osteotomy fixation device of claim 8, wherein the second surface transmits compressive loads experienced by the device to the distal plate.

10. The internal osteotomy fixation device of claim 9, wherein the ratchet arm further comprises an oval-shaped through hole in a distal portion, and a major axis of the oval is aligned with the first axis.

11. The internal osteotomy fixation device of claim 8, further comprising a proximal plate.

12. The internal osteotomy fixation device of claim 11, wherein the proximal plate is hingedly connected to the slide.

13. An internal osteotomy fixation device, comprising:
    a distal plate including a channel;
    a slide slidably received within the channel such that the slide is translatable with respect to the distal plate along a first axis, the slide having a segment of ratchet teeth on a first surface, the segment having a first length; and
    a ratchet arm fixed to the distal plate, the ratchet arm including teeth configured to engage the slide ratchet teeth, the ratchet arm having a second length;
    wherein in a completely retracted configuration, the segment overlaps the ratchet arm such that an overall length of the device is dependent upon the longer of the first length or the second length.

14. The internal osteotomy fixation device of claim 13, further comprising a proximal plate.

15. The internal osteotomy fixation device of claim 14, wherein the proximal plate is hingedly connected to the slide.

16. An internal osteotomy fixation device, comprising:
    a distal plate including a channel;
    a slide slidably received within the channel such that the slide is translatable with respect to the distal plate along a first axis, the slide having ratchet teeth on a first surface;
    a ratchet arm fixed to the distal plate in a cantilevered fashion, the ratchet arm including teeth configured to engage the slide ratchet teeth; and
    the distal plate further comprises a through-hole, and a release tool is insertable within the through-hole to engage the ratchet arm.

17. The internal osteotomy fixation device of claim 16, wherein rotation of the release tool within the through-hole flexes the ratchet arm and disengages the ratchet arm teeth from the slide teeth.

18. The internal osteotomy fixation device of claim 16, wherein the distal plate further comprises a beveled portion surrounding a medial side of the through-hole, and the beveled portion is configured to guide the release tool toward the through-hole.

19. The internal osteotomy fixation device of claim 16, further comprising a proximal plate.

20. The internal osteotomy fixation device of claim 19, wherein the proximal plate is hingedly connected to the slide.

21. An internal osteotomy fixation device, comprising:
    a proximal plate including a channel;
    a slide slidably received within the channel such that the slide is translatable with respect to the proximal plate along a first axis, the slide having ratchet teeth on a first surface; and
    a ratchet arm fixed to the proximal plate, the ratchet arm including teeth configured to engage the slide ratchet teeth;
    wherein a cross-sectional area of the ratchet arm decreases from a proximal end of the ratchet arm toward a distal end of the ratchet arm.

22. The internal osteotomy fixation device of claim 21, wherein the ratchet arm is configured to maintain a constant stress level along a flexed portion of the ratchet arm.

23. The internal osteotomy fixation device of claim 21, further comprising a distal plate.

24. The internal osteotomy fixation device of claim 23, wherein the distal plate is hingedly connected to the slide.

* * * * *